United States Patent
Joshi-Hangal et al.

(10) Patent No.: US 10,485,764 B2
(45) Date of Patent: Nov. 26, 2019

(54) LYOPHILIZED PHARMACEUTICAL COMPOSITIONS

(71) Applicant: Otsuka Pharmaceutical Co., Ltd., Tokyo (JP)

(72) Inventors: Rajashree Joshi-Hangal, Pleasanton, CA (US); Sanjeev Redkar, San Ramon, CA (US)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 332 days.

(21) Appl. No.: 15/200,086

(22) Filed: Jul. 1, 2016

(65) Prior Publication Data

US 2017/0000738 A1    Jan. 5, 2017

Related U.S. Application Data

(60) Provisional application No. 62/188,025, filed on Jul. 2, 2015.

(51) Int. Cl.
| | | |
|---|---|---|
| *A61K 31/7084* | (2006.01) | |
| *C07H 21/04* | (2006.01) | |
| *A61K 9/19* | (2006.01) | |
| *F26B 5/06* | (2006.01) | |
| *A61K 47/20* | (2006.01) | |

(52) U.S. Cl.
CPC ............ *A61K 9/19* (2013.01); *A61K 31/7084* (2013.01); *A61K 47/20* (2013.01); *C07H 21/04* (2013.01); *F26B 5/06* (2013.01)

(58) Field of Classification Search
CPC .......... A61K 9/19; A61K 31/7084; F26B 5/06
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 4,690,918 A | 9/1987 | Beppu et al. |
| 4,837,028 A | 6/1989 | Allen |
| 4,855,304 A | 8/1989 | Devash |
| 5,013,556 A | 5/1991 | Woodle et al. |
| 5,157,120 A | 10/1992 | Ogilvie |
| 5,213,804 A | 5/1993 | Martin et al. |
| 5,225,212 A | 7/1993 | Martin et al. |
| 5,264,221 A | 11/1993 | Tagawa et al. |
| 5,356,633 A | 10/1994 | Woodle et al. |
| 5,540,935 A | 7/1996 | Miyazaki et al. |
| 5,543,152 A | 8/1996 | Webb et al. |
| 5,556,948 A | 9/1996 | Tagawa et al. |
| 5,607,691 A | 3/1997 | Hale et al. |
| 5,665,710 A | 9/1997 | Rahman et al. |
| 5,736,531 A | 4/1998 | Von Borstel et al. |
| 5,770,713 A | 6/1998 | Imbach et al. |
| 5,856,090 A | 1/1999 | Epstein |
| 5,968,914 A | 10/1999 | Von Borstel et al. |
| 6,136,791 A | 10/2000 | Nyce |
| 6,153,383 A | 11/2000 | Verdine et al. |
| 6,432,924 B1 | 8/2002 | Nyce |
| 6,472,521 B1 | 10/2002 | Uhlmann et al. |
| 6,900,301 B2 | 5/2005 | Cook et al. |
| 6,900,540 B1 | 5/2005 | Teig et al. |
| 6,905,669 B2 | 6/2005 | Dimartino |
| 6,982,253 B2 * | 1/2006 | Joshi-Hangal ....... A61K 9/0019 514/42 |
| 6,998,391 B2 | 2/2006 | Lyons et al. |
| 7,135,464 B2 | 11/2006 | Joshi-Hangal et al. |
| 7,144,873 B2 * | 12/2006 | Joshi-Hangal ....... A61K 9/0019 514/49 |
| 7,250,416 B2 | 7/2007 | Phiasivongsa et al. |
| 7,276,228 B2 | 10/2007 | DiMartino |
| 7,700,567 B2 | 4/2010 | Phiasivongsa et al. |
| 8,461,123 B2 | 6/2013 | Phiasivongsa et al. |
| 9,358,248 B2 | 6/2016 | Phiasivongsa et al. |
| 9,381,207 B2 * | 7/2016 | Joshi-Hangal ....... A61K 9/0019 |
| 9,480,698 B2 | 11/2016 | Phiasivongsa et al. |
| 9,913,856 B2 * | 3/2018 | Joshi-Hangal ....... A61K 9/0019 |
| 2001/0012835 A1 | 8/2001 | Fine et al. |

(Continued)

FOREIGN PATENT DOCUMENTS

| | | |
|---|---|---|
| CN | 101282986 A | 10/2008 |
| CN | 101361718 A | 2/2009 |

(Continued)

OTHER PUBLICATIONS

Searles et al., "Annealing to optimize the primary drying rate, reduce freezing-induced drying rate heterogeneity, and determine T' in pharmaceutical lyophilization" Journal of Pharmaceutical Sciences / vol. 90, Issue 7, pp. 1-33 (Year: 2001).*
Co-pending U.S. Appl. No. 15/879,802, filed Jan. 25, 2018.
Notice of allowance dated Dec. 14, 2017 for U.S. Appl. No. 15/174,386.
Office action dated Oct. 19, 2017 for U.S. Appl. No. 14/771,011.
Robert, et al. Ipilimumab plus dacarbazine for previously untreated metastatic melanoma. N Engl J Med. Jun. 30, 2011;364(26):2517-26.
Ansel, Howard C, et al. Pharmaceutical Dosage Forms and Drug Delivery Systems. Philadelphia, PA: Lippincott-Williams & Wilkins, 1999. Print.
Avino, A. et al. Preparation and Properties of Oligodeoxynucleotides Containing 4-O-Butylthymine, 2-Fluorohypoxanthine and 5-Azacytosine. Bioorganic & Medicinal Chemistry Letters. 1995; 5(20): 2331-2336.

(Continued)

*Primary Examiner* — Eric Olson
(74) *Attorney, Agent, or Firm* — Wilson Sonsini Goodrich & Rosati

(57) ABSTRACT

The invention provides a method of preparing a lyophilized pharmaceutical composition containing a dinucleotide compound or a pharmaceutically-acceptable salt thereof. The process comprises dissolving the dinucleotide compound in a solvent comprising dimethylsulfoxide and optionally one or more co-solvents to form a solution, and then removing the solvent and any co-solvents by a freeze-drying process. Also provided by the invention are lyophilized pharmaceutical compositions and their use in medicine and in particular in the treatment of cancer.

36 Claims, 1 Drawing Sheet

(56) References Cited

U.S. PATENT DOCUMENTS

| | | |
|---|---|---|
| 2002/0114809 A1 | 8/2002 | Rubinfeld et al. |
| 2003/0039689 A1 | 2/2003 | Chen et al. |
| 2003/0045497 A1 | 3/2003 | Widegren et al. |
| 2003/0108588 A1 | 6/2003 | Chen et al. |
| 2003/0147813 A1 | 8/2003 | Lyons |
| 2003/0158598 A1 | 8/2003 | Ashton et al. |
| 2003/0229047 A1 | 12/2003 | Joshi-Hangal et al. |
| 2004/0019036 A1 | 1/2004 | Robin et al. |
| 2004/0052864 A1 | 3/2004 | Rubinfeld et al. |
| 2004/0109846 A1 | 6/2004 | Rubinfeld et al. |
| 2004/0162263 A1 | 8/2004 | Sands et al. |
| 2004/0224919 A1 | 11/2004 | Rubinfeld et al. |
| 2005/0037992 A1 | 2/2005 | Lyons et al. |
| 2005/0059682 A1 | 3/2005 | Rubinfeld |
| 2005/0159375 A1 | 7/2005 | Srivastava et al. |
| 2005/0209186 A1 | 9/2005 | Lyons |
| 2005/0266012 A1 | 12/2005 | Andrieu et al. |
| 2006/0014949 A1 | 1/2006 | Redkar et al. |
| 2006/0063735 A1 | 3/2006 | Redkar et al. |
| 2006/0069060 A1 | 3/2006 | Redkar et al. |
| 2006/0074046 A1 | 4/2006 | Redkar et al. |
| 2006/0128653 A1 | 6/2006 | Tang et al. |
| 2006/0128654 A1 | 6/2006 | Tang et al. |
| 2006/0140947 A1 | 6/2006 | Lyons et al. |
| 2006/0205687 A1 | 9/2006 | Phiasivongsa et al. |
| 2007/0072796 A1 | 3/2007 | Phiasivongsa et al. |
| 2007/0105792 A1 | 5/2007 | DiMartino |
| 2007/0117776 A1 | 5/2007 | Lyons |
| 2007/0254835 A1 | 11/2007 | Lyons et al. |
| 2008/0108559 A1 | 5/2008 | DiMartino |
| 2010/0062992 A1 | 3/2010 | Redkar et al. |
| 2010/0215729 A1 | 8/2010 | Phiasivongsa et al. |
| 2013/0236536 A1 | 9/2013 | Phiasivongsa et al. |
| 2014/0303107 A1 | 10/2014 | Joshi-Hangal et al. |
| 2016/0015805 A1 | 1/2016 | Azab et al. |
| 2016/0130296 A1 | 5/2016 | Phiasivongsa et al. |
| 2016/0346310 A1 | 12/2016 | Joshi-Hangal et al. |
| 2017/0035794 A1 | 2/2017 | Phiasivongsa et al. |
| 2018/0369267 A1* | 12/2018 | Joshi-Hangal ....... A61K 31/708 |

FOREIGN PATENT DOCUMENTS

| | | |
|---|---|---|
| CS | 269077 B1 | 4/1990 |
| DE | 1922702 A1 | 11/1969 |
| DE | 2105468 A1 | 11/1971 |
| EP | 0251464 A2 | 1/1988 |
| EP | 0286958 A2 | 10/1988 |
| EP | 0334368 A2 | 9/1989 |
| EP | 0393575 B1 | 3/1994 |
| EP | 0496813 B1 | 12/1994 |
| EP | 0515156 B1 | 2/1996 |
| JP | H05219974 A | 8/1993 |
| JP | H05246891 A | 9/1993 |
| JP | 2001163776 A | 6/2001 |
| JP | 2002223753 A | 8/2002 |
| JP | 2002370939 A | 12/2002 |
| JP | 2003310293 A | 11/2003 |
| JP | 5030958 B2 | 9/2012 |
| WO | WO-8804924 A1 | 7/1988 |
| WO | WO-8909779 A1 | 10/1989 |
| WO | WO-9004384 A1 | 5/1990 |
| WO | WO-9105545 A1 | 5/1991 |
| WO | WO-9301202 A1 | 1/1993 |
| WO | WO-9307295 A1 | 4/1993 |
| WO | WO-9324510 A1 | 12/1993 |
| WO | WO-9420073 A1 | 9/1994 |
| WO | WO-9426761 A1 | 11/1994 |
| WO | WO-9426764 A1 | 11/1994 |
| WO | WO-9427632 A1 | 12/1994 |
| WO | WO-9515373 A2 | 6/1995 |
| WO | WO-9610391 A1 | 4/1996 |
| WO | WO-9611280 A1 | 4/1996 |
| WO | WO-9636693 A1 | 11/1996 |
| WO | WO-9639035 A1 | 12/1996 |
| WO | WO-9640062 A1 | 12/1996 |
| WO | WO-9640165 A1 | 12/1996 |
| WO | WO-9704787 A1 | 2/1997 |
| WO | WO-9713499 A1 | 4/1997 |
| WO | WO-9723230 A1 | 7/1997 |
| WO | WO-9816186 A2 | 4/1998 |
| WO | WO-9940188 A2 | 8/1999 |
| WO | WO-0023112 A1 | 4/2000 |
| WO | WO-0037504 A2 | 6/2000 |
| WO | WO-0040269 A2 | 7/2000 |
| WO | WO-0062075 A1 | 10/2000 |
| WO | WO-0074634 A2 | 12/2000 |
| WO | WO-0114424 A2 | 3/2001 |
| WO | WO-0129235 A2 | 4/2001 |
| WO | WO-0169262 A1 | 9/2001 |
| WO | WO-0221140 A1 | 3/2002 |
| WO | WO-02053138 A2 | 7/2002 |
| WO | WO-02057425 A2 | 7/2002 |
| WO | WO-02069903 A2 | 9/2002 |
| WO | WO-02076486 A2 | 10/2002 |
| WO | WO-02083705 A1 | 10/2002 |
| WO | WO-02085400 A1 | 10/2002 |
| WO | WO-02087586 A1 | 11/2002 |
| WO | WO-02094859 A2 | 11/2002 |
| WO | WO-02101353 A2 | 12/2002 |
| WO | WO-03012085 A1 | 2/2003 |
| WO | WO-03012112 A1 | 2/2003 |
| WO | WO-03020252 A2 | 3/2003 |
| WO | WO-03026574 A2 | 4/2003 |
| WO | WO-03031932 A2 | 4/2003 |
| WO | WO-03040363 A1 | 5/2003 |
| WO | WO-03043631 A2 | 5/2003 |
| WO | WO-03045427 A2 | 6/2003 |
| WO | WO-03046190 A1 | 6/2003 |
| WO | WO-03062826 A2 | 7/2003 |
| WO | WO-03065995 A2 | 8/2003 |
| WO | WO-03076660 A1 | 9/2003 |
| WO | WO-03092623 A2 | 11/2003 |
| WO | WO-03103687 A1 | 12/2003 |
| WO | WO-03104427 A2 | 12/2003 |
| WO | WO-2005032475 A2 | 4/2005 |
| WO | WO-2006048749 A1 | 5/2006 |
| WO | WO-2006063111 A2 | 6/2006 |
| WO | WO-2006071491 A1 | 7/2006 |
| WO | WO-2006071983 A2 | 7/2006 |
| WO | WO-2006099132 A1 | 9/2006 |
| WO | WO-2006116713 A1 | 11/2006 |
| WO | WO-2006121168 A1 | 11/2006 |
| WO | WO-2007005874 A2 | 1/2007 |
| WO | WO-2007041071 A2 | 4/2007 |
| WO | WO-2011128642 A1 | 10/2011 |
| WO | WO-2012033953 A1 | 3/2012 |
| WO | WO-2012140627 A1 | 10/2012 |
| WO | WO-2013033176 A1 | 3/2013 |
| WO | WO-2013117969 A1 | 8/2013 |
| WO | WO-2014134355 A1 | 9/2014 |
| WO | WO-2017004538 | 1/2017 |

OTHER PUBLICATIONS

Barnette, W. E. N-Fluoro-N-alkylsulfonamides: Useful Reagents for the Fluorination of Carbanions. J. Am. Chem. Soc. 1984; 106:452-454.

Baylin, et al. Alterations in DNA Methylation: a Fundamental Aspect of Neoplasia. Cancer Res. 1998; 72:141-196.

Bigey, P. et al. Modified Ologonucleotides as Bona Fide Antagonists of Proteins Interacting with DNA. The Journal of Biological Chemistry. 1999; 274(8): 4594-4606.

Bouchard, et al. Incorporation of 5-Aza-2'-deoxycytidine-5'-triphosphate into DNA. Interactions with mammalian DNA polymerase alpha and DNA methylase. Mol. Pharmacol. 1983; 24: 109-14.

Brank, A. S. et al. Inhibition of Hhal DNA (Cytosine-C5) Methyltransferase by Oligodeoxyribonucleotides Containg 5-Aza-2'-deoxycytidine: Examination of the Intertwined Roles of Cofactor, Target, Transition State Structure and Enzyme Conformation. J. Mol. Biol. 2002; 323: 53-67.

Brown, R. et al. Demethylation of DNA by decitabine in cancer chemotherapy. Expert Rev Anticancer Ther. 2004; 4(4): 501-510.

(56) References Cited

OTHER PUBLICATIONS

Chabot, et al. Kinetics of deamination of 5-aza-2'-deoxycytidine and cytosine arabinoside by human liver cytidine deaminase and its inhibition by 3-deazauridine, thymidine or uracil arabinoside. Biochemical Pharmacology. 1983; 32:1327-1328.
Commercon, et al. Substitution of vinylic iodides by various copper(I) and copper (II) derivatives. J. Organometallic Chem. 1975; 93:415-421.
Co-pending U.S. Appl. No. 12/498,223, filed Jul. 6, 2009.
Co-pending U.S. Appl. No. 15/174,386, filed Jun. 6, 2016.
Co-pending U.S. Appl. No. 15/200,086, filed Jul. 1, 2016.
Co-pending U.S. Appl. No. 15/278,550, filed Sep. 28, 2016.
Co-pending U.S. Appl. No. 90/013,682, filed Jan. 19, 2016.
Coral, et al., "Immunomodul a tory activity of SGI-118, a 5-aza-2'-deoxycytidine-containing demethylating dinucleotide", Cancer Immunology, Immunotherapy, Nov. 9, 2012, 1(62): 605-614.
Darkin-Rattray, et al. Apicidin: A novel antiprotozoal agent that inhibits parasite histone deacetylase. PNAS, 1996, 93: (23) 13143-13147.
Daskalakis, et al. Expression of a Hypermethylated and Silenced P15/INK4B Gene in a Subgroup of MDS Patients is Restored by Treatment With the Methylation Inhibitor 5-AZA-2'-Deoxycytidine. Abstracts Leukemia Research. 2001; Suppl. No. 1:S16-S17.
Dax, et al. Synthesis of deoxyfluoro sugars from carbohydrate precursors. Carbohydr Res. 2000; 327:47-86.
Desimone, et al. Maintenance of elevated fetal hemoglobin levels by decitabine during dose interval treatment of sickle cell anemia. Blood. 2002; 99(11):3905-8.
Digiacomo, et al., Ipilimumab experience in heavily pretreated patients with melanoma in an expanded access program at the University Hospital of Siena (Italy), Cancer immunol immunotherapy, Apr. 2011, 60:467-77.
Eritja, et al. Synthesis and properties of oligonucleotides containing 5-AZA-2'-deoxycytidine. Nucleosides and Nucleotides. 1997; 16(7-9):1111-114.
Esteller, M. A Gene Hypermethylation Profile of Human Cancer. Cancer Research. 2001; 61:3225-3229.
Esteller, M. CpG Island Hypermethylation and Tumor Suppressor Genes: A Booming Present, a Brighter Future. Oncogene. 2002; 21:5427-5440.
Esteller, M. Epigenetic Lesions Causing Genetic Lesions in Human Cancer: Promoter Hypermethylation of DNA Repair Genes. European Journal of Cancer. 2000; 36:2294-2300.
European search report and opinion dated Jul. 15, 2013 for EP Application No. 06804123.5.
European search report and search opinion dated Sep. 18, 2015 for EP Application No. EP15161013-6.
Fernández, et al. Synthesis of 2-Deoxy-3,5-di-O-benzoyl-2,2-difluoro-D-ribose from D-Glucose and D-Mannose. A Formal Synthesis of Gemcitabine. Tetrahedron. 1998; 54:3523-3532.
Yoshida, et al. Potent and specific inhibition of mammalian histone deacetylase both in vivo and in vitro by trichostatin A. J Biol Chem. Oct. 5, 1990;265(28):17174-9.
Zhenodarova, et al. Nucleoside antimetabolites in the synthesis of the internucleotide bond catalyzed by ribonucleases. Nukleazy: Biol. Rol Prakt. Ispol'z. ( 1985 ), 25-8. Editor(s): Berdyshev, G. D.; Khursin, N. E. Publisher: Naukova Dumka, Kiev, USSR. Coden: 54IIAL, 1985 (in Russian with English).
Francis, et al. Reaction of tetrahydrofolic acid with cyanate from urea solutions: formation of an inactive folate derivative. Am. J. Clin. Nutr. 1977; 30:2028-2032.
Gagnon, et al. Interaction of 5-aza-2'-deoxycytidine and Depsipeptide on Antineoplastic Activity and Activation of 14-3-3σ, E-Cadherin and Tissue Inhibitor of Metalloproteinase 3 Expression in Human Breast Carcinoma Cells. Anti-Cancer Drugs. 2003; 14(3):193-202.
Garcia, R. G. et al. Synthesis of Oligonucleotide Inhibitors of DNA (Cytosine-C5) Methyltransferase Containing 5-Azacytosine Residues at Specific Sites. Antisense & Nucleic ACID Drg Development. 2001; 11: 369-378.

Gilbert, J. et al. The Clinical Application of Targeting Cancer through Histone Acetylation and Hypomethylation. Clinical Cancer Research. 2004; 10: 4589-4596.
Glick et al. Hybrid Polar Histone Deacetylase Inhibitor Induces Apoptosis and CD95/CD95 Ligand Expression in Human Neuroblastoma.
Hanna, Naeem B. et. al. Synthesis of some 6-substituted 5-azacytidines. Collect. Czech. Chem. Commun. 1998; 63:222-230.
Heikkila, et al. Synthesis of adenylyl-(3'----5')-guanosine and some analogues as probes to explore the molecular mechanism of stimulation of influenza virus RNA polymerase. Acta Chem Scand B. 1985;39(8):657-69.
Herman, J. G. et al. Gene Silencing in Cancer in Association with Promoter Hypermethylation. The New England Journal of Medicine. 2003; 349(21): 2042-2054.
Hodi, et al., Improved Survival with Ipilimumab in Patients with Metastatic Melanoma, N Engl J Med, Aug. 19, 2010, 363:711-23.
Honda, et al. RNA polymerase of influenza virus. Dinucleotide-primed initiation of transcription at specific positions on viral RNA. J Biol Chem. May 5, 1986;261(13):5987-91.
International search report and written opinion dated Jul. 27, 2007 for PCT/US2006/037313.
International search report and written opinion dated Sep. 16, 2016 for PCT Application No. PCT/US2016/040730.
International search report and written opinion dated Nov. 7, 2012 for PCT/US2012/052816.
International Search Report dated Aug. 7, 2014 for PCT US2014019137.
Issa, et al. Phase 1 study of low-dose prolonged exposure schedules of the hypomethylating agent 5-aza-2'-deoxycytidine (decitabine) in hematopoietic malignancies. Blood. 2004; 103(5): 1635-40.
Issa, J.P. Decitabine. Current Opinion in Oncology. 2003; 15(6): 446-451.
Iupac Compendium of Chemical Terminology—glycosyl. IUPAC Pure and Applied Chemistry. 1995; 67:1338.
Iwai, et al., Involvement of PD-L1 on tumor cells in the escape from host immune system and tumor immunotherapy by PD-L1 blockade, Proc Natl Acad Sci USA, Sep. 17, 2002, 99: 12293-12297.
Jones, et al. The Fundamental Role of Epigenetic Events in Cancer. Nature Reviews/Genetics. 2002; 3:415-428.
Jones, et al. The Role of DNA Methylation in Cancer. Adv. Cancer Res. 1990; 54:1-23.
Jones, P. A. DNA methylation and cancer. Oncogene. 2002; 21:5358-5360.
Juttermann, et al. Toxicity of 5-aza-2'-deoxycytidine to mammalian cells is mediated primarily by covalent trapping of DNA methyltransferase rather than DNA demethylation. Proc Natl Acad Sci U S A. 1994; 91:11797-11801.
Karpf, et al. Reactivating the Expression of Methylation Silenced Genes in Human Cancer. Oncogene. 2002; 21:5496-5503.
Kijima, et al. Trapoxin, an antitumor cyclic tetrapeptide, is an irreversible inhibitor of mammalian histone deacetylase. J Biol Chem. Oct. 25, 1993;268(30):22429-35.
Kissinger, et al. Determination of the antileukemia agents cytarabine and azacitidine and their respective degradation products by high-performance liquid chromatography. J. Chromat. 1986; 353:309-318.
Koblish, et al. Hydroxyamidine Inhibitors of Indoleamine-2, 3-dioxygenase Potently Suppress Systemic Tryptophan Catabolism and the Growth of IDO-Expressing Tumors. Mol Cancer Ther, vol. 9 No. 2 pp. 489-498.
Kwon, et al. Depudecin induces morphological reversion of transformed fibroblasts via the inhibition of histone deacetylase. Proc Natl Acad Sci U S A. Mar. 31, 1998;95(7):3356-61.
La Rosee, et al. In Vitro Efficacy of Combined Treatment Depends on the Underlying Mechanism of Resistance in Imatinib-Resistant Bcr-Abl positive Cell Lines. Blood First Edition Paper. prepublished online 2003; DOI 10.1182/blood-2003-04-1074, pp. 1-39.
Leach, et al., Enhancement of Antitumor Immunity by CTLA-4 Blockade, Science 1996, 271:1734-1736.
Leone, G. et al. DNA methylation and demethylating drugs in myelodysplastic syndromes and secondary leukemias. Haematologica. 2002; 87(12): 1324-1341.

(56) References Cited

OTHER PUBLICATIONS

Leone, G. et al. Inhibitors of DNA methylation in the treatment of hematological malignancies and MDS. Clin Immunol. 2003; 109(1): 89-102.
Lieberman, et al. Pharmaceutical Dosage Forms, Tablets. New York: M. Dekker, 1980. Print.
Lin, K.S. et al. High-Performance Liquid Chromatographic Analysis of Chemical Stability of 5-Aza-2'-deoxycytidine. Journal of Pharmaceutical Sciences. 1981; 70(11): 1228-1232.
McIntosh, et al. Synthesis and characterization of poly[d(G-aza5C)] B-Z transition and inhibition of DNA methylase. Biochemistry. 1985; 24(18):4806-4814.
Mojaverian, et al. Development of an intravenous formulation for the unstable investigational cytotoxic nucleosides 5-azacytosine arabinoside (NSC 281272) and 5-azacytidine (NSC 102816). J. Pharm. Pharmacol. 1984; 36:728-733.
Momparler, et al. Molecular, cellular and animal pharmacology of 5-aza-2'-deoxycytidine. Pharmacol Ther. 1985; 30:287-99.
Nephew, et al. Epigenetic gene silencing in cancer initiation and progression. Cancer Letters. 2003; 190:125-133.
Notice of allowance dated Feb. 12, 2016 for U.S. Appl. No. 13/894,288.
Notice of allowance dated Feb. 15, 2013 for U.S. Appl. No. 12/703,096.
Notice of allowance dated Mar. 2, 2016 for U.S. Appl. No. 13/894,288.
Notice of allowance dated Mar. 7, 2016 for U.S. Appl. No. 14/241,635.
Notice of allowance dated Jul. 1, 2016 for U.S. Appl. No. 14/979,148.
Notice of allowance dated Sep. 25, 2015 for U.S. Appl. No. 13/894,288.
Notice of allowance dated Nov. 23, 2015 for U.S. Appl. No. 14/241,635.
Notice of allowance dated Dec. 4, 2009 for U.S. Appl. No. 11/241,799.
"O' Day, et al. Targeting Cytotoxic T-Lymphocyte Antigen (CTLA-4), A Novel Strategy for the Treatment of Melanoma and Other Malignancies. Cancer, vol. 110 No. 12 pp. 2614-2627".
Office action dated Jan. 9, 2008 for U.S. Appl. No. 11/241,799.
Office action dated Feb. 23, 2016 for U.S. Appl. No. 14/979,148.
Office action dated Mar. 16, 2016 for U.S. Appl. No. 90/013,682.
Office action dated Mar. 30, 2009 for U.S. Appl. No. 11/241,799.
Office action dated May 30, 2007 for U.S. Appl. No. 11/241,799.
Office action dated Jul. 30, 2015 for U.S. Appl. No. 14/241,635.
Office action dated Aug. 19, 2008 for U.S. Appl. No. 11/241,799.
Office action dated Nov. 1, 2012 for U.S. Appl. No. 12/703,096.
Palmisano, et al. In-cell indirect electrochemical halogenation of pyrimidine bases and their nucleosides to 5-haloderivatives. Tetrahedron Lett. 1992; 33(50): 7779-7782.
Pankiewiz, K. W. Fluorinated nucleosides. Carbohydr. Res. 2000; 327:87-105.
Paz, et al. A Systematic Profile of DNA Methylation in Human Cancer Cell Lines. Cancer Research. 2003; 63:1114-1121.
Piskala, et al. Direct synthesis of 5 azapyrimidine 2'-deoxyribonucleosides. Hydrolysis of 5-aza-2'-deoxycytidine. Nucleic Acids Res. 1978; 4:s109-s113.
Pliml, et al. Synthesis of a 2-deoxy-D-ribofuranosyl-5-azacytosine. Collect. Czech. Chem. Commun. 1964; 29:2576-2577.
Pompon, et al. Reversed-phase high-performance liquid chromatography of nucleoside analogues. Simultaneous analysis of anomeric D-xylo- and D-lyxofuranonucleosides and some other D-pentofuranonucleosides. J. Chromat. 1987; 388: 113-22.
Primeau, et al. Synergistic Antineoplastic Action of DNA Methylation Inhibitor 5-AZA-2'-Deoxycytidine and Histone Deacetylase Inhibitor Depsipeptide on Human Breast Carcinoma Cells. Int. J. Cancer. 2003; 103:177-184.
Remington, et al. Remington's Pharmaceutical Sciences. Easton, PA: Mack Pub., 1990. Print.
Remington, et al. Remington: The Science and Practice of Pharmacy. Easton, PA: Mack Pub., 1995. Print.
Santini, et al. Changes in DNA Methylation in Neoplasia: Pathophysiology and Therapeutic Implications. Annals of Internal Medicine. 2001; 134:573-586.
Schrump, et al. Phase 1 Study of Sequential Deoxyazacytidine/Depsipeptide Infusion in Patients With Malignancies Involving Lungs or Pleura. Clinical Lung Cancer. 2002; 186-192.
Schwartz, et al. Six new saddle-shaped hosts based on fused dibenzofuran units. J. Am. Chem. Soc. 1992; 114:10775-10784.
Search report dated Feb. 4, 2015 for SG Application No. 2014013395.
Shaker, et al. Preclinical evaluation of antineoplastic activity of inhibitors of DNA methylation (5OazaO2'-deoxycytidine) and histone deacetylation (trichostatin A, depsipeptide) in combination against myeloid leukemic cells. Leukemia Research. 2003; 27:437-444.
Sheikhnejad, et al. Mechanism of inhibition of DNA (cytosine C5)-methyltransferases by oligodeoxyribonucleotides containing 5,6-dihydro-5-azacytosine. J Mol Biol. Feb. 5, 1999;285(5):2021-34.
Smiraglia, et al. The Study of Aberrant Methylation in Cancer via Restriction Landmark Genomic Scanning. Oncogene. 2002; 21:5414-5426.
Steinhagen, et al., TLR-Based Immune Adjuvants, Vaccine, Apr. 12, 2011, 29(17): 3341-3355.
Sucher, et al., IDO-Mediated Tryptophan Degradation in the pathogenesis of Malignant Tumor Disease, International Journal of Tryptophan Research, 2010: 3, 113-120.
Topalian, et al.,Safety, Activity, and Immune Correlates of Ant-PD-1 Antibody in Cancer, N Engl J Med. Jun. 28, 2012, 366, 2443-2454.
Tsang, et al. Hydrophobic Cluster Formation Is Necessary for Dibenzofuran-Based Amino Acids to Function as β-Sheet Nucleators. J. Am. Chem. Soc. 1994; 116:3988-4005.
Tsuji, et al. A new antifungal antibiotic, trichostatin. J Antibiot (Tokyo) Jan. 1976; 29(1): 1-6.
Zhong, et al. Dinucleotide analogues as novel inhibitors of RNA-dependent RNA polymerase of hepatitis C Virus. Antimicrob Agents Chemother. Aug. 2003;47(8):2674-81.
Von Hoff, et al. 5-Azacytidine. A New Anticancer Drug With Effectiveness in Acute Myelogenous Leukemia. Annals of Internal Medicine. 1976; 85(2): 237-45.
Wajed, et al. DNA Methylation: An Alternative Pathway to Cancer. Annals of Surgery 2001; 234(1):10-20.
Weber, et al., Immune Checkpoint Proteins: A New Therapeutic Paradigm for Cancer-Preclinical Background: CTLA-4 and PD-1 Blockade, Oct. 2010, 37:430-439.
Weiser, et al. Sequential 5-aza-2'-deoxycytidine-depsipeptide FR901228 treatment induces apoptosis preferentially in cancer cells and facilities their recognition by cytolytic T lymphocytes specific for NY-ESO-1. Journal of Immunotherapy. 2001; 24(2):151-161.
Written opinion dated Jul. 16, 2015 for SG Application No. 2014013395.
Xiong, et al. COBRA: a sensitive and quantitative DNA methylation assay. Nucleic Acids Res. 1997; 25:2532-2534.
Office action dated Jun. 16, 2015 for U.S. Appl. No. 13/894,288.
Chuang, et al. S110, a 5-Aza-2'-deoxycytidine—containing dinucleotide, is an effective DNA methylation inhibitor in vivo and can reduce tumor growth. Molecular cancer therapeutics 9.5 (2010): 1443-1450.
Office action dated May 26, 2017 for U.S. Appl. No. 15/174,386.
Carducci M., et al. Phenylbutyrate (PB) for refractory solid tumors: Phase I clinical and pharmacologic evaluation of intravenous and oral PB. Anticancer Res., 17: 3972-3973, 1997.
Gupta, V. Das. Effect of Ethanol, Glycerol, and Propylene Glycol on the Stability of Phenobarbital Sodium. Journal of Pharmaceutical Sciences, Nov. 1984. vol. 73, No. 11; 1661-1662.
Lee, et al. Stereospecific synthesis of alkenyl fluorides (with retention) via organometallic intermediates. J. Am. Chem. Soc. 1986; 108:2445-2447.
Maio, et al. Molecular Pathways: At the Crossroads of Cancer Epigenetics and Immunotherapy. Clin Cancer Res. Sep. 2015; 4040-4047.
Sigalotti, et al. Epigenetic drugs as immunomodulators for Combination Therapies in Solid Tumors. Pharmacology & Therapeutics. 2014; 142; 339-350.
Strickley, Robert G. Solubilizing Excipients in Oral and Injectable Formulations. Pharmaceutical Research. Feb. 2004; vol. 21, No. 2; 201-230.

(56) References Cited

OTHER PUBLICATIONS

Wrangle, et al. Alterations of Immune Response of Non-Small Cell Lung Cancer with Azacytidine. Oncotarget, 2013; 4: 2067-2079.
Yang, et al. Expression of PD-L1, PD-L2, PD-1 and CTLA4 in Myelodysplastic Syndromes is Enhanced by Treatment with Hypomethylating Agents. Leukemia. Jun. 2014; 28(6) 1280-1288.
Allen, et al. Large unilamellar liposomes with low uptake into the reticuloendothelial system. FEBS Lett. Oct. 19, 1987;223(1):42-6.
Alul, et al. Oxalyl-CPG: a labile support for synthesis of sensitive oligonucleotide derivatives. Nucleic Acids Res. Apr. 11, 1991;19(7):1527-32.
Bagnall, et al. New inhalation anaesthetics: II. Fluorinated methyl propyl ethers. Journal of Fluorine Chemistry. 1978; 11(2):93-107.
Bayer, et al. Liquid phase synthesis of peptides. Nature. Jun. 30, 1972;237(5357):512-3.
Beaucage, et al. Deoxynucleoside Phosphoramidites—a new class of key intermediates for Deoxypolynucleotide synthesis. Tetrahedron Lett. 1981; 22:1859-1862.
Berge, et al. Pharmaceutical salts. J Pharm Sci. Jan. 1977;66(1):1-19.
Blume, et al. Liposomes for the sustained drug release in vivo. Biochim Biophys Acta. Nov. 2, 1990;1029(1):91-7.
Bonora. Polyethylene glycol: a high-efficiency liquid phase (HELP) for the large-scale synthesis of the oligonucleotides. Appl Biochem Biotechnol. 1995; 54: 3-17.
Boyes, et al. Regulation of activity of the transcription factor GATA-1 by acetylation. Nature. Dec. 10, 1998;396(6711):594-8.
Brehm, et al. Retinoblastoma protein recruits histone deacetylase to repress transcription. Nature. Feb. 5, 1998;391(6667):597-601.
Carducci, et al. Phenylbutyrate (PB) for refractory solid tumors: Phase I clinical and pharmacologic evaluation of intravenous an doral PB. Anticancer Res. 1997; 17:3972-3973.
Co-pending U.S. Appl. No. 16/053,354, filed Aug. 2, 2018.
Coral et al. 5-AZA-2'-Deoxycytidine in Cancer Immunotherapy: A Mouse to Man Story. Cancer Res 2007. 67:(6) 2900.
Coral, et al. 5-AZA-2'Deoxycytidine-induced Expression of Functional Cancer Testis Antigens in Human Renal Cell Carcinoma: Immunotherapeutic Implications. Clin Cancer Res. Aug. 2002; vol. 8; 2690-2695.
Coral, et al. Immunomodulatory activity of SGI-110, a 5-AZA-2'-deoxycytidine-containing demethylating dinucleotide. 2010. Poster.
Coral, et al. Immunomodulatory activity of SGI-110, a 5-aza-2'-deoxycytidine-containing demethylating dinucleotide. Poster.
Coral, et al. Immunomodulatory activity of SGI-110, a 5-aza-2'-deoxycytidine-containing demethylating dinucleotide. RT-PCR Analysis of CTA. Poster.
Coral, et al. Phenotypic and Functional Changes of Human Melanoma Xenografts Induced by DNA Hypomethylation: Immunotherapeutic Implications. Journal of Cellular Physiology. 2006; 207:58-66.
Covre, et al. Epigenetic immunomodulation by SGI-110 combined with immune check-point blockade as a new therapeutic strategy. Poster.
Cruz, et al. Improving T-cell Therapy for Relapsed EBV-Negative Hodgkin Lymphoma by Targeting Upregulated MAGE-A4. Clin Cancer Res. 2011; 17: 7058-7066.
Darkin-Rattray, et al. Apicidin: a novel antiprotozoal agent that inhibits parasite histone deacetylase. Proc. Natl. Acad. Sci. USA. 1996; 93:13143-13147.
Das Gupta, V. Effect of ethanol, glycerol, and propylene glycol on the stability of phenobarbital sodium. J Pharm Sci. Nov. 1984;73(11):1661-2.
European Serial No. 18177788.9 Extended Search Report dated Jan. 4, 2019.
Fonsatti, et al. Functional Up-regulation of Human Leukocyte Antigen Class I Antigens Expression by 5-aza-2'-deoxycytidine in Cutaneous Melanoma: Immunotherapeutic Implications. Clin Cancer Res. 2007; 13(11) 3333-3338.
Gabizon, et al. Liposome formulations with prolonged circulation time in blood and enhanced uptake by tumors. Proc Natl Acad Sci U S A. Sep. 1988;85(18):6949-53.
Glick, et al. Hybrid polar histone deacetylase inhibitor induces apoptosis and CD95/CD95 ligand expression in human neuroblastoma. Cancer Res. Sep. 1, 1999;59(17):4392-9.
Gu, et al. Activation of p53 sequence-specific DNA binding by acetylation of the p53 C-terminal domain. Cell. Aug. 22, 1997;90(4):595-606.
Newmark, et al. Butyrate as a differentiating agent: pharmacokinetics, analogues and current status. Cancer Lett. Apr. 1, 1994;78(1-3):1-5.
Saito, et al. A synthetic inhibitor of histone deacetylase, MS-27-275, with marked in vivo antitumor activity against human tumors. Proc. Natl Acad Sci U S A. Apr. 13, 1999;96(8):4592-7.
U.S. Appl. No. 14/771,011 Final Office Action dated Jan. 18, 2019.
U.S. Appl. No. 14/771,011 Office Action dated Jun. 13, 2018.

* cited by examiner

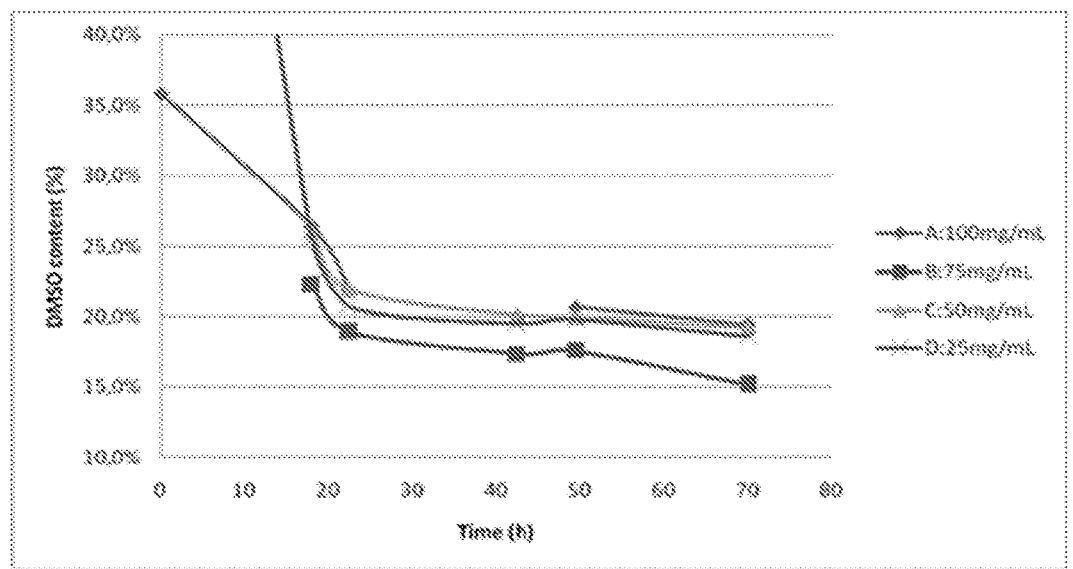

LYOPHILIZED PHARMACEUTICAL COMPOSITIONS

CROSS REFERENCE

This Application claims the benefit of U.S. Provisional Application No. 62/188,025, filed Jul. 2, 2015, which is incorporated herein by reference in its entirety.

BACKGROUND

DNA methylation is a post replicative chemical modification of DNA. Different cancers can be stratified by their abnormal DNA methylation profiles (degree of global or specific DNA methylation) and the hypermethylation of specific genes can be associated with the prognosis for gastric, lung, esophageal, pancreatic, and colon cancer. DNA methylation patterns can also be used to predict response or resistance to therapy in glioma and melanoma. Azacitidine and decitabine are two FDA approved hypomethylating agents (HMAs) that exert their therapeutic effect by inhibiting DNA methylation levels.

Dinucleotide compounds derived from decitabine for the development of therapies for similar indications have been described in U.S. Pat. No. 7,700,567 and its equivalent WO2007041071. Drug formulations containing dinucleotide compounds of the type described in WO2007041071 are disclosed in WO2013033176. The disclosure in each of U.S. Pat. No. 7,700,567, WO2007041071 and WO2013033176 is incorporated by reference in its entirety.

Lyophilization, often referred to as freeze drying, is a method of dehydration in which a solvent-containing substrate is frozen and then subjected to a vacuum so that the solvent is removed by sublimation, i.e. direct conversion from the the solid frozen state into the gaseous state.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method of preparing a lyophilized pharmaceutical composition, the method comprising dissolving a compound of formula (1):

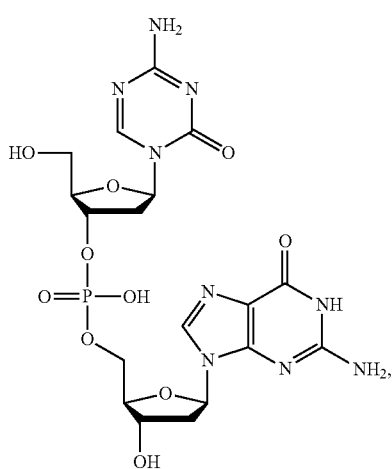

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature thereof to a temperature of no greater than about −20° C.; (ii) a first warming stage in which the temperature of the frozen solution is raised to a temperature in the range from about −15° C. to about 5° C., wherein the temperature in the range from about −15° C. to about 5° C. keeps the solution frozen; (iii) a second freezing stage in which the temperature of the solution is lowered to a temperature of no greater than about −20° C.; (iv) a primary drying stage, wherein the primary drying stage comprises a sublimation step in which the DMSO is removed by sublimation from the solution in its frozen state under reduced pressure to give a partially dried product; and (v) a secondary drying stage in which the DMSO is removed by evaporation from the partially dried product in a non-frozen state under reduced pressure to give the lyophilized product.

In some embodiments, the invention provides a pharmaceutical composition prepared by a process comprising the steps of: dissolving a compound of formula (1):

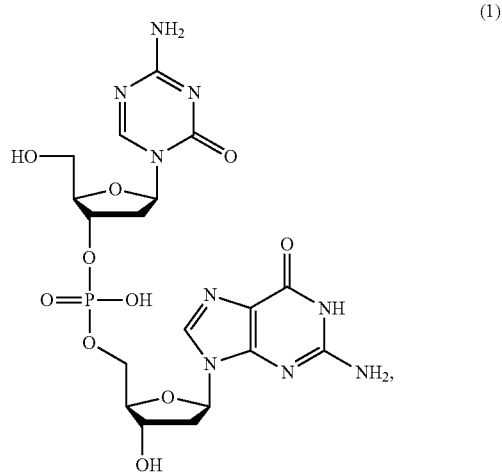

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature thereof to a temperature of no greater than about −20° C.; (ii) a first warming stage in which the temperature of the frozen solution is raised to a temperature in the range from about −15° C. to about 5° C., wherein the temperature in the range from about −15° C. to about 5° C. keeps the solution frozen; (iii) a second freezing stage in which the temperature of the solution is lowered to a temperature of no greater than about −20° C.; (iv) a primary drying stage, wherein the primary drying stage comprises a sublimation step in which the DMSO is removed by sublimation from the solution in its frozen state under reduced pressure to give a partially dried product; and (v) a secondary drying stage in which the DMSO is removed by evaporation from the partially dried product in a non-frozen state under reduced pressure to give the lyophilized product.

BRIEF DESCRIPTION OF THE FIGURES

FIG. 1 is a plot of DMSO removal with time as the lyophilization process of the invention progresses. DMSO removal profiles for four formulations A, B, C and D of different concentrations are shown in FIG. 1.

DETAILED DESCRIPTION

This application relates to lyophilized pharmaceutical compositions containing a dinucleotide derived from decitabine and to methods for the preparation and use of decitabine-derived dinucleotide compositions.

The present invention relates to improved lyophilized compositions containing a compound of formula (1) or a pharmaceutically acceptable salt thereof, and to a method of preparing the improved lyophilized pharmaceutical compositions using a freeze drying process. The invention also provides the use of the lyophilized pharmaceutical compositions in medicine and in particular their use in the treatment of cancers.

The present disclosure provides improved methods for lyophilization of a substrate comprising a non-aqueous solvent, for example, DMSO and a compound of formula (1), or a pharmaceutically-acceptable salt thereof. Generally, the methods involve two freezing stages with an intermediate warming stage (annealing stage) between the two freezing stages. The methods can be used for removal of the non-aqueous solvent from the substrate. In some particular embodiments, the compound within the substrate is a compound of formula (1):

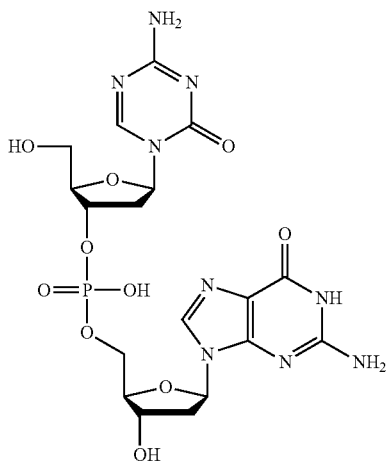

or a pharmaceutically acceptable salt thereof. The present disclosure also provides lyophilized compositions comprising a compound of formula (1) or a pharmaceutically acceptable salt thereof. In addition, the present disclosure provides uses of the lyophilized pharmaceutical compositions in medicine, particularly in the treatment of cancers.

It has been found that by using two freezing stages and an intermediate warming stage (annealing stage) between the two freezing stages, DMSO can be removed much more quickly during the subsequent primary drying stage and that, consequently, the length of the secondary drying stage can be significantly reduced. Without wishing to be bound by any theory, it is believed that the intermediate warming stage can provide increased porosity, thereby enabling the DMSO to sublime more readily. Thus, much more of the DMSO is removed during the primary drying stage.

Freeze Drying Microscopy (FDM) studies on the formulations have shown that, even at temperatures below −30° C., on occasion, there can be some residual non-frozen solvent or co-solvent present. The term "frozen" as used herein therefore includes a state in which there is present a solid structure formed from solvent and/or co-solvent molecules but there can also be present some solvent and/or co-solvent in non-frozen, or liquid, form.

Method for Preparing Lypophilized Pharmaceutical Composition.

The methods provided herein include a method of preparing a lyophilized pharmaceutical composition comprising a compound, for example, a compound of formula (1)) or a pharmaceutically-acceptable salt thereof, which method comprises dissolving the compound of formula (1) or the pharmaceutically acceptable salt thereof in a non-aqueous solvent comprising dimethylsulfoxide and optionally one or more co-solvents to form a solution, and then removing the solvent and any co-solvents by a freeze-drying process to give a lyophilized product; wherein the freeze-drying process comprises one or more of the following stages: (i) a first freezing stage in which the solution is frozen by reducing the temperature thereof to a temperature of no greater than −20° C.; (ii) a first warming stage in which the temperature of the frozen solution is raised to a temperature in the range from −15° C. to 5° C. at which the solution remains in a frozen state; (iii) a second freezing stage, which occurs after the first warming stage and in which the temperature of the solution in its frozen state is lowered to a temperature of no greater than −20° C.; (iv) a primary drying stage comprising a sublimation step in which dimethylsulfoxide and one or more co-solvents when present are removed by sublimation from the solution in its frozen state under reduced pressure to give a partially dried product; and (v) a secondary drying stage in which dimethylsulfoxide and one or more co-solvents when present are removed by evaporation from the partially dried product in a non-frozen state under reduced pressure to give the lyophilized product.

The sequence of freezing and intermediate warming stages (i), (ii), and (iii) can be repeated one or more times before proceeding to the primary drying stage (iv). For example, a first sequence of stages (i), (ii), and (iii) can be followed by a second sequence of stages (i), (ii), and (iii), and optionally by third and fourth sequences of stages (i), (ii), and (iii) before proceeding to the primary drying stage (iv).

The method of the invention can, for example, reduce the overall time for the freeze-drying process by at least a day and, in some embodiments of the invention, by up to two days. The method of the invention can further allow reconstitution of the solution more readily than compositions prepared using methods that omit the intermediate warming stage. For example, in some embodiments of the invention as defined herein, the reconstitution time of the compositions can be reduced from a time in excess of 30 minutes to a time of less than 20 minutes and, in some embodiments, a time of less than 10 minutes.

The freeze-drying procedure can be carried out in a lyophilization apparatus. The lyophilization apparatus can have a chamber in which lyophilization containers (e.g. lyophilization vials) containing solution can be placed for freeze-drying. The chamber can be connected to a vacuum source (e.g. a vacuum pump) to enable the pressure within the chamber to be reduced. The apparatus can also have components for freezing or heating the contents of the chamber. Prior to freeze-drying, a bulk solution of the compound of formula (1) in DMSO and optionally one or more co-solvents can be prepared and filtered through a filter (e.g. a sterilising filter) before aliquots are filled into lyophilization containers (e.g. lyophilization vials) and transferred to the lyophilization apparatus. Prior to transfer to the lyophilization apparatus, the containers can be partially stoppered to prevent contamination but still permit escape of the solvent during the freeze-drying process.

In the following paragraphs, parameters of the freeze-drying process are set out in more detail with reference to particular embodiments, sets, subsets, ranges and individual values for each parameter. For the avoidance of doubt, each embodiment, set, subset, range and individual value defined in relation to one parameter of the freeze-drying process can be combined with each embodiment, set, subset, range and individual value defined in relation to any other parameter of the freeze-drying process. This application therefore discloses all combinations of the embodiments, sets, subsets, ranges and individual values for each parameter of the freeze-drying process.

The temperatures referred to above and elsewhere herein in relation to the parameters of the lyophilization process are the temperatures of the shelves in the lyophilization apparatus. The shelves are typically cooled by cooling fluids, the temperatures of which are monitored and provide a method of determining the shelf temperatures. The temperature measurements obtained from the cooling fluids can be cross-checked against temperatures obtained directly from the product in the lyophilization containers by inserting temperature probes into selected lyophilization containers.

In the first freezing stage (i), the solution can be frozen by reducing the temperature thereof to a temperature of no greater than about −20° C., for example, the temperature can be reduced to a value of no greater than about −30° C. (or no greater than about −35° C., or no greater than about −40° C., or no greater than about −41° C., or no greater than about −42° C., or no greater than about −43° C., or no greater than about −44° C.). For example, the solution can be frozen by reducing the temperature to a value in the range from about −40° C. to about −50° C., or about −42° C. to about −48° C., or about −43° C. to about −47° C., or about −44° C. to about −46° C., e.g. at about −45° C.

The first freezing stage can involve a temperature ramping step wherein the temperature is reduced from an initial (e.g. ambient) temperature to a target temperature over a first time period, for example over a period of up to about 2 hours or up to about 1.5 hours or up to 1.25 hours, e.g. about 1 hour.

Once the target temperature has been reached, the frozen solution can be held at the target temperature for a second time period, for example up to about 3 hours, or up to about 2.5 hours or up to about 2 hours, e.g. about 1.5 hours.

Following the first freezing stage, the solution can be subjected to a first warming stage in which the temperature of the frozen solution is raised to a temperature in the range −15° C. and 4° C. at which the solution remains in a frozen state. For example, the frozen solution can be warmed to a temperature in the range from about −5° C. to about 5° C., or from about −3° C. to about 3° C., or from about −2° C. to about 2° C., or from about −1° C. to about 1° C., for example at about 0° C.

The first warming stage can involve a first time period over which the frozen solution is warmed to a target temperature and a second time period over which the frozen solute is held at the target temperature. For example, the first time period over which the frozen solution is warmed to a target temperature can be up to about 2 hours, or up to about 1.75 hours, or up to about 1.5 hours, for example, about 1.3 hours.

Following the first warming stage, the still-frozen solution can be subjected to a second freezing stage in which the temperature of the solution in its frozen state is lowered to a temperature of no greater than about −20° C. The temperature can be reduced to a value of no greater than about −30° C. (or no greater than about −35° C., or no greater than about −40° C., or no greater than about −41° C., or no greater than about −42° C., or no greater than about −43° C., or no greater than about 44° C.). For example, the temperature of the frozen solution can be reduced to a value in the range from about −40° C. to about −50° C., or about −42° C. to about −48° C., or about −43° C. to about −47° C., or about −44° C. to about −46° C., for example, at about −45° C.

After the second freezing stage, the frozen solution can be subjected to a primary drying stage comprising a sublimation step in which dimethylsulfoxide and one or more co-solvents when present are removed by sublimation from the solution in its frozen state under reduced pressure to give a partially dried product. In the primary drying stage, the frozen solution can be warmed to facilitate faster sublimation of the DMSO, whilst maintaining the solution in a frozen state. For example, the frozen solution can be warmed to a temperature in the range from −25° C. to 0° C., or from −22° C. to −2° C., e.g. from about −20° C. to about −5° C.

In the primary drying stage, the frozen solution can be warmed in steps. For example, in a first warming step, the temperature can be raised from a temperature of no greater than about −30° C. to a temperature in the range from about −25° C. to about −19° C. (e.g. about −20° C.), and then held at that temperature for a defined holding period. At this temperature, residual unfrozen solvent and/or co-solvent can be removed by evaporation.

In a second warming step the temperature can be raised from a temperature in the range from about −25° C. to about −19° C. (e.g. about −20° C.), to a temperature in the range from about −10° C. to about 0° C. (e.g. about −5° C.) and then held at that temperature for further defined holding period. It will be appreciated that further intermediate warming stages and holding periods can be added to the first and second warming stages. As an alternative to warming the frozen solution in stages, warming can be carried out in a continuous manner until a required target temperature is attained.

At the beginning of the primary drying period, the pressure in the vessel containing the frozen solution can be reduced (typically from atmospheric pressure) to a pressure at which removal of the DMSO and optionally other co-solvents can take place. The pressure can be reduced to a pressure of lower than 1 mBar, for example, below 500 µBar, or less than 100 µBar, or less than 50 µBar. For example, the pressure can be reduced to a pressure of less than 20 µBar, or less than 10 µBar, or from 1 to 10 µBar, or from 4 to 8 µBar, e.g. about 6 µBar.

The primary drying stage can involve an initial pressure-reducing stage in which the temperature is held constant and the pressure is reduced to a target value, followed by warming of the frozen solution as defined above. Alternatively, the reduction in pressure and the warming of the frozen solution can be carried out simultaneously.

The primary drying stage can take from about 20 to about 60 hours, for example, from about 30 to about 50 hours.

The progress of the primary drying stage can be monitored by one or more sensors or gauges present in a lyophilization chamber of the lyophilization apparatus. The sensors or gauges (such as a Pirani gauge) can be used to measure one or more parameters within the chamber, whereby defined changes in the one or more parameters can indicate the progress of the primary drying and provide a means of determining when sublimation of DMSO and optionally any co-solvents has been completed. For example, a sensor or gauge can measure pressure within the chamber or the conductivity of gas in the chamber.

During the sublimation process, the temperature must be below the critical temperature and pressure of the product so that the product remains frozen. Sublimation is a direct solid-to-gas DMSO phase change. If the conditions are above the critical temperature and pressure, the product is not frozen and, instead, is a liquid and the DMSO can change from a liquid-to-gas (boils). It is disadvantageous for the DMSO to boil instead of sublime.

The primary drying stage can be performed under pressures of from about 5 µBar to about 40 µBar. The freezing temperature of the product at these pressures is about −2° C. to about −4° C. The primary drying stage can be performed at temperatures from about −3° C. to about −9° C. At this temperature range, the vapor pressure is adequate for a quick sublimation, which leads to a better product. In some embodiments, the pressure is about 20 µBar. In some embodiments, the temperature is about −6° C.

Once sublimation of the DMSO has ceased, or has fallen below a certain level, the secondary drying stage is initiated. In the secondary drying stage, dimethylsulfoxide and one or more co-solvents when present are removed by evaporation from the partially dried product in a non-frozen state under reduced pressure to give a lyophilized product. Thus, in the secondary drying stage, a reduced pressure environment is maintained and the partially dried product is heated to a temperature at which it is no longer frozen. As the boiling point of DMSO is about 189° C., the partially dried product can be heated to a temperature of at least about 40° C., more usually at least about 45° C., for example at least about 50° C., or at least about 55° C. In some embodiments, the partially dried product is heated to a temperature in the range from about 55° C. to about 70° C., for example, about 65° C.

The secondary drying stage can involve one or more temperature ramping steps in which the partially dried product is heated to a target temperature, each temperature ramping step being followed by a temperature holding step. In one embodiment, there is a single temperature ramping step followed by a single temperature holding step.

During the secondary drying stage, unfrozen solvent molecules are removed to give a lyophilized product containing only low levels of residual DMSO.

It is advantageous for the secondary drying stage to be performed at a temperature of about 30° C. to about 65° C., for example, about 40° C.

At the end of the secondary drying stage, an inert gas such as nitrogen is admitted into the lyophilization chamber and the containers (e.g. vials) containing the lyophilized product are fully sealed (e.g. by means of stopper and optionally also a cap) under inert gas.

The freeze-drying procedure can be carried out on a solution of a compound of the formula (1) or a pharmaceutically acceptable salt thereof in a non-aqueous solvent comprising dimethylsulfoxide and optionally one or more co-solvents.

In some embodiments, water contamination is avoided at any stage. Without being bound by theory, it is believed that hydrate formation particularly disrupts the product's structure that becomes not conducive to easy reconstitution.

In some embodiments of the invention, substantially no co-solvents are present; i.e. the solvent consists essentially of DMSO.

In other embodiments of the invention, one or more of the other non-aqueous co-solvents can be present. Where a co-solvent is present, the total volume of co-solvent can typically constitute no more than about 25% (v/v) of the total solvent. More usually, the total volume of co-solvent, when present, constitutes no more than about 20%, or no more than about 15%, or no more than about 10%, or no more than about 5% by volume of the total volume of solvent. For example, the total volume of co-solvent, can constitute from about 0% (v/v) to about 5% (v/v) of the total volume of solvent.

The solution to be lyophilized can contain an amount of the compound of formula (1) or the pharmaceutically acceptable salt thereof in the range from about 5 mg/ml to about 200 mg/ml, for example, in the range from about 10 mg/ml to about 150 mg/ml. For example, the solution can contain from about 20 mg/ml to about 120 mg/ml, or from about 22 mg/ml to about 110 mg/ml, or from about 25 mg/ml to about 105 mg/ml, or from about 25 mg/ml to about 100 mg/ml of the compound of formula (1) or the pharmaceutically acceptable salt thereof.

In some embodiments, the solution contains from about 40 mg/ml to about 110 mg/ml, or from about 50 mg/ml to about 105 mg/ml of the compound of formula (1) or the pharmaceutically acceptable salt thereof.

In a particular embodiment of the invention, the solution contains either 75 mg/ml; or 100 mg/ml of a sodium salt of the compound of formula (1).

Non-limiting examples of pressures that can be used during a method of the invention include about 1 µBar, about 2 µBar, about 3 µBar, about 4 µBar, about 5 µBar, about 6 µBar, about 7 µBar, about 8 µBar, about 9 µBar, about 10 µBar, about 15 µBar, about 20 µBar, about 25 µBar, about 30 µBar, about 35 µBar, about 40 µBar, about 45 µBar, about 50 µBar, about 55 µBar, about 60 µBar, about 65 µBar, about 70 µBar, about 80 µBar, about 90 µBar, and about 100 µBar.

Lyophilized Pharmaceutical Compositions.

The invention provides a lyophilized pharmaceutical composition, which is preparable by (or prepared by) a freeze-drying process as described herein.

The lyophilized pharmaceutical compositions of the invention are characterized by enhanced solubility relative to known lyophilized formulations of compounds of the formula (1) and their salts. Accordingly, in another embodiment, the invention provides a lyophilized pharmaceutical composition comprising a compound of formula (1) or a pharmaceutically acceptable salt thereof, which is obtainable by a freeze-drying process as defined herein and which has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than 20 minutes.

In some embodiments, the lyophilized pharmaceutical composition has a dissolution time in the non-aqueous solvent of no greater than 15 minutes, or no greater than 12 minutes.

In particular embodiments, the lyophilized pharmaceutical composition has a dissolution time in the non-aqueous solvent of no greater than 10 minutes.

The lyophilized pharmaceutical compositions of the invention are also characterised by reduced levels of residual DMSO solvent. Accordingly, in another embodiment, the invention provides a lyophilized pharmaceutical composition comprising a compound of formula (1) or a pharmaceutically acceptable salt thereof, which is obtainable by a freeze-drying process as defined herein and wherein, in an amount of lyophilized composition obtained from 1 gram of solution, there is a residual DMSO content of no greater than 20 mg, or no greater than 19 mg. It will be appreciated that the reference to "solution" means the solution of the pharmaceutically acceptable salt thereof in a solvent comprising dimethylsulfoxide and optionally one or more co-solvents. The solvent can be non-aqueous, anhydrous or substantially-anhydrous.

In another embodiment, there is provided a lyophilized pharmaceutical composition comprising a compound of formula (1) or a pharmaceutically acceptable salt thereof, which is obtainable by a freeze-drying process as defined herein and wherein any residual DMSO is present in the composition in an amount corresponding to no more than 35 mg per 100 mg equivalent of the free base of the compound of formula (1).

The term "100 mg equivalent of the free base" refers to the amount by weight of free base that can be present or, when the compound of formula (1) is in the form of a salt, to the amount by weight of the free base contained within the salt. For example, the amount of residual DMSO per 100 mg equivalent of the free base is no more than about 32 mg, or no more than about 31 mg, for example in the range from about 15 mg to about 35 mg, or from about 20 mg to about 32 mg, or from about 25 mg to about 30 mg.

In another embodiment, there is provided a lyophilized pharmaceutical composition comprising a compound of formula (1) or a pharmaceutically acceptable salt thereof, which is obtainable by a freeze-drying process as defined herein and which: (a) has a dissolution time, at ambient temperature, and without the aid of mechanised stirring, in a solvent containing 65% (v/v) propylene glycol; 25% (v/v) glycerine; and 10% (v/v) ethanol, of no greater than 20 minutes (or no greater than 15, or 12 or 10 minutes); and (b) has a residual DMSO content such that, in an amount of lyophilized composition obtained from 1 gram of solution, the residual DMSO content is no greater than 20 mg, or no greater than 19 mg. The solvent can be non-aqueous, anhydrous or substantially-anhydrous.

The lyophilized pharmaceutical compositions of the invention, i.e. the compositions obtainable by the freeze-drying process as defined herein, can also be characterised with regard to their enhanced porosity, and increased specific surface area compared to known compositions. The specific surface area can be measured using known techniques such as the Brunauer-Emmett-Teller (BET) adsorption method.

The lyophilized pharmaceutical compositions of the invention can be provided in sealed containers such as vials (e.g. glass vials), optionally containing a protective atmosphere of an inert gas such as nitrogen or argon. The sealed containers can be opened when required and the contents reconstituted by dissolving in a reconstitution solvent, such as a non-aqueous, anhydrous or substantially-anhydrous solvent, prior to administration to a patient. Examples of solvents in which the lyophilized pharmaceutical compositions of the invention can be reconstituted are disclosed in WO2013033176.

In a further aspect therefore, the invention provides a sealed pharmaceutical container containing a lyophilized pharmaceutical composition as defined herein. The sealed pharmaceutical container can be, for example, a vial fitted with a stopper and optionally additional components (such as a collar) for holding the stopper in place. The sealed container can optionally contain a protective atmosphere of an inert gas such as nitrogen or argon.

In a particular embodiment, the invention provides a sealed pharmaceutical container containing a lyophilized pharmaceutical composition as defined herein wherein the composition contains the compound of formula (1) or a pharmaceutically acceptable salt thereof in an amount corresponding to approximately 100 mg equivalent of the free base of the compound of formula (1), and wherein no more than 35 mg of residual DMSO is present in the composition.

Reconstituted Formulations Prepared from the Lyophilized Pharmaceutical Compositions.

The lyophilized pharmaceutical compositions of the invention can be reconstituted in solvents, such as non-aqueous, anhydrous or substantially-anhydrous solvents, to give injectable liquid compositions for administration to a subject. The liquid compositions can be for administration by subcutaneous injection. Accordingly, in a further aspect, the invention provides a method for preparing an injectable liquid composition, which method comprises dissolving a lyophilized pharmaceutical composition as defined herein in a solvent, particularly a non-aqueous solvent.

Non-limiting examples of suitable solvents include propylene glycol, glycerin, ethanol, and any combination of the foregoing. The formulations can be prepared as non-aqueous formulations. The formulations can be anhydrous or substantially anhydrous.

A mixture of solvents can contain a percentage of propylene glycol on either a mass or a volume basis. In some embodiments, the percentage of propylene glycol can be at least about 10%, at least about 20%, at least about 30%, at least about 40%, at least about 50%, at least about 10%, at least about 20%, at least about 30%, at least about 40%, or at least about 50%. In some embodiments, the percentage of propylene glycol can be at most 90%, at most 80%, at most 70%, at most 60%, at most about 90%, at most about 80%, at most about 70%, or at most about 60%. In some embodiments, the percentage of propylene glycol can be about 30% to about 90%, about 45% to about 85%, about 55% to about 75%, about 60% to about 70%, about 30% to about 90%, about 45% to about 85%, about 55% to about 75%, or about 60% to about 70%. In some embodiments, the percentage of propylene glycol can be 30%, 35%, 40%, 45%, 50%, 55%, 60%, 65%, 70%, 75%, 80%, 85%, 90%, about 30%, about 35%, about 40%, about 45%, about 50%, about 55%, about 60%, about 65%, about 70%, about 75%, about 80%, about 85%, or about 90%.

A mixture of solvents can contain a percentage of glycerin on either a mass or a volume basis. In some embodiments, the percentage of glycerin can be at least 5%, at least 10%, at least 15%, at least 25%, at least 30%, at least about 5%, at least about 10%, at least about 15%, at least about 25%, or at least about 30%. In some embodiments, the percentage of glycerin can be at most 70%, at most 60%, at most 50%, at most 40%, at most 30%, at most about 70%, at most about 60%, at most about 50%, at most about 40%, or at most about 30%. In some embodiments, the percentage of glycerin can be 0% to 50%, 5% to 45%, 15% to 35%, 20% to 30%, 0% to about 50%, about 5% to about 45%, about 15% to about 35%, or about 20% to about 30%. In some embodiments, the percentage of glycerin can be 0%, 5%, 10%, 15%, 20%, 25%, 30%, 35%, 40%, 45%, 50%, about 5%, about 10%, about 15%, about 20%, about 25%, about 30%, about 35%, about 40%, about 45%, or about 50%.

A mixture of solvents can contain a percentage of ethanol on either a mass or a volume basis. In some embodiments, the percentage of ethanol can be at least 1%, at least 3%, at least 5%, at least 10%, at least 15%, at least about 1%, at least about 3%, at least about 5%, at least about 10%, or at least about 15%. In some embodiments, the percentage of ethanol can be at most 30%, at most 25%, at most 20%, at most 15%, at most 10%, at most about 30%, at most about 25%, at most about 20%, at most about 15%, or at most about 10%. In some embodiments, the percentage of ethanol can be 0% to 30%, 0% to 25%, 0% to 20%, 5% to 15%, 0% to about 30%, 0% to about 25%, 0% to about 20%, or about 5% to about 15%. In some embodiments, the percentage of ethanol can be 0%, 1%, 2%, 3%, 4%, 5%, 6%, 7%, 8%, 9%, 10%, 11%, 12%, 13%, 14%, 15%, about 1%, about 2%, about 3%, about 4%, about 5%, about 6%, about 7%, about 8%, about 9%, about 10%, about 11%, about 12%, about 13%, about 14%, or about 15%.

In some embodiments, a solvent or a mixture of solvents comprises 45% to 85% propylene glycol, 5% to 45% glycerin, and 0% to 30% ethanol. In some embodiments, a solvent or a mixture of solvents comprises about 45% to about 85% propylene glycol, about 5% to about 45% glycerin, and 0% to about 30% ethanol. In some embodiments, a solvent or a mixture of solvents consists essentially of 45% to 85% propylene glycol, 5% to 45% glycerin, and 0% to 30% ethanol. In some embodiments, a solvent or a mixture of solvents consists essentially of about 45% to about 85% propylene glycol, about 5% to about 45% glycerin, and 0% to about 30% ethanol. In some embodiments, a solvent or a mixture of solvents is 45% to 85% propylene glycol, 5% to 45% glycerin, and 0% to 30% ethanol. In some embodiments, a solvent or a mixture of solvents is about 45% to about 85% propylene glycol, about 5% to about 45% glycerin, and 0% to about 30% ethanol.

In some embodiments, a solvent or a mixture of solvents comprises 55% to 75% propylene glycol, 15% to 35% glycerin, and 0% to 20% ethanol. In some embodiments, a solvent or a mixture of solvents comprises about 55% to about 75% propylene glycol, about 15% to about 35% glycerin, and 0% to about 20% ethanol. In some embodiments, a solvent or a mixture of solvents consists essentially of 55% to 75% propylene glycol, 15% to 35% glycerin, and 0% to 20% ethanol. In some embodiments, a solvent or a mixture of solvents consists essentially of about 55% to about 75% propylene glycol, about 15% to about 35% glycerin, and 0% to about 20% ethanol. In some embodiments, a solvent or a mixture of solvents is 55% to 75% propylene glycol, 15% to 35% glycerin, and 0% to 20% ethanol. In some embodiments, a solvent or a mixture of solvents is about 55% to about 75% propylene glycol, about 15% to about 35% glycerin, and 0% to about 20% ethanol.

In some embodiments, a solvent or a mixture of solvents comprises 60% to 70% propylene glycol; 20% to 30% glycerin; and 5% to 15% ethanol. In some embodiments, a solvent or a mixture of solvents comprises about 60% to about 70% propylene glycol; about 20% to about 30% glycerin; and about 5% to about 15% ethanol. In some embodiments, a solvent or a mixture of solvents consists essentially of 60% to 70% propylene glycol; 20% to 30% glycerin; and 5% to 15% ethanol. In some embodiments, a solvent or a mixture of solvents consists essentially of about 60% to about 70% propylene glycol; about 20% to about 30% glycerin; and about 5% to about 15% ethanol. In some embodiments, a solvent or a mixture of solvents is 60% to 70% propylene glycol; 20% to 30% glycerin; and 5% to 15% ethanol. In some embodiments, a solvent or a mixture of solvents is about 60% to about 70% propylene glycol; about 20% to about 30% glycerin; and about 5% to about 15% ethanol.

In some embodiments, a solvent or a mixture of solvents comprises 65% propylene glycol; 25% glycerin; and 10% ethanol. In some embodiments, a solvent or a mixture of solvents comprises about 65% propylene glycol; about 25% glycerin; and about 10% ethanol. In some embodiments, a solvent or a mixture of solvents consists essentially of 65% propylene glycol; 25% glycerin; and 10% ethanol. In some embodiments, a solvent or a mixture of solvents consists essentially of about 65% propylene glycol; about 25% glycerin; and about 10% ethanol. In some embodiments, a solvent or a mixture of solvents is 65% propylene glycol; 25% glycerin; and 10% ethanol. In some embodiments, a solvent or a mixture of solvents is about 65% propylene glycol; about 25% glycerin; and about 10% ethanol.

Excipients.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, and suspensions, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, 0.9% saline, or 5% dextrose in water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use in the invention include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a decitabine derivative dinucleotide, or a pharmaceutically acceptable salt thereof, in combination with a pharmaceutically acceptable carrier. The carrier can be selected to minimize any degradation of the active ingredient and to minimize any adverse side effects in the subject.

The compound of formula (I) or a pharmaceutically acceptable salt thereof herein can be conveniently formulated into pharmaceutical compositions composed of one or more pharmaceutically acceptable carriers. See e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as, saline and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include, but are not limited to, saline, Ringer's solution and dextrose solution. The pH of the solution can be from about 5 to about 8, and can be from about 7 to about 7.5. Further carriers include sustained release preparations such as semipermeable matrices of solid hydrophobic polymers containing the compound of formula (I) or a pharmaceutically-acceptable salt thereof, where the matrices are in the form of shaped articles, e.g., films, liposomes, microparticles, or microcapsules.

The disclosed methods relate to administering the compound of formula (I) or a pharmaceutically acceptable salt thereof as part of a pharmaceutical composition. In various embodiments, compositions of the invention can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, and anesthetics.

An excipient can fill a role as simple and direct as being an inert filler, or an excipient as used herein can be part of a pH stabilizing system or coating to insure delivery of the ingredients safely to the stomach.

The compound of formula (I) or a pharmaceutically-acceptable salt thereof can also be present in liquids, emulsions, or suspensions for delivery of active therapeutic agents in aerosol form to cavities of the body such as the nose, throat, or bronchial passages. The ratio of the compound of formula (I) or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, for example, in unit dosage form suitable for single administration of a precise dosage. The compositions can contain, as noted above, an effective amount of the compound of formula (I) or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Pharmaceutically Acceptable Salts.

The compound of formula (1) and the pharmaceutically acceptable salts thereof can be prepared by the methods described in WO2013033176 and as described below in the Examples.

In each of the foregoing aspects and embodiments of the invention, the compound of formula (1) can be used in the form of a salt or a non-salt.

Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt. In some embodiments, a pharmaceutically-acceptable salt is an ammonium salt.

Acid addition salts can arise from the addition of an acid to a compound described herein. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

One particular example of a salt of the compound of formula (1) is a sodium salt.

Therapeutic Uses.

The lyophilized pharmaceutical compositions according to the present invention can be used to treat a wide variety of diseases that are sensitive to the treatment with decitabine, including those described herein.

Accordingly, in other aspects, the invention provides: (i) a lyophilized pharmaceutical composition as defined herein for use in medicine; (ii) a lyophilized pharmaceutical composition as defined herein for use in the treatment of a disease as defined herein; (iii) a method of treating a disease as defined herein, which method comprises mixing a lyophilized pharmaceutical composition as defined herein with a pharmaceutically acceptable solvent and administering an effective amount of the mixture to a subject in need thereof; (iv) the use of a lyophilized pharmaceutical composition as defined herein for the manufacture of a medicament for the treatment of a disease as defined herein; (v) a method of treating cancer in a patient in need thereof, which method comprises reconstituting the lyophilized pharmaceutical composition as defined herein in a pharmaceutically acceptable solvent to give a liquid formulation containing a compound of formula (1) or a pharmaceutically acceptable salt thereof, and administering a therapeutically effective amount of the liquid formulation to the patient.

Examples of diseases that can be treated using the lyophilized pharmaceutical compositions of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Examples of cancers are carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Specific types of cancers or malignant tumors, either primary or secondary, that can be treated using this invention include bladder cancer, breast cancer, ovarian cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

In one embodiment, the cancer is selected from myelodysplastic syndrome, acute myelogenous leukaemia, ovarian cancer, liver cancer, and colorectal cancer.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Treatment of abnormal cell proliferation due to insults to body tissue during surgery can be possible for a variety of surgical procedures, including joint surgery, bowel surgery, and cheloid scarring. Diseases that produce fibrotic tissue include emphysema.

Repetitive motion disorders that can be treated using the present invention include carpal tunnel syndrome. An example of cell proliferative disorders that can be treated using the invention is a bone tumor.

The proliferative responses associated with organ transplantation that can be treated using this invention include those proliferative responses contributing to potential organ rejections or associated complications. Specifically, these proliferative responses can occur during transplantation of the heart, lung, liver, kidney, and other body organs or organ systems.

Abnormal angiogenesis that can be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In some embodiments, the lyophilized pharmaceutical compositions of the present invention can be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases can depend on the severity of the condition, the route of administration, and related factors that can be decided by the attending physician. Generally, accepted and effective daily doses are the amount sufficient to effectively inhibit angiogenesis and/or angiogenic diseases.

The lyophilized pharmaceutical compositions of the present invention can be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In some embodiments, the lyophilized pharmaceutical compositions of the present invention can be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state Inhibition of angiogenesis using the pharmaceutical formulations of the present invention can prevent the formation of the granulomas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but can also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract Inhibition of angiogenesis by the lyophilized pharmaceutical compositions of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the lyophilized pharmaceutical compositions of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention can reduce the likelihood of the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis can actively contribute to, and help maintain, the chronically inflamed state of rheumatoid arthritis. Treatment using the pharmaceutical formulations of the present invention alone or in conjunction with other anti-RA agents can reduce the likelihood of the formation of new blood vessels necessary to maintain the chronic inflammation and provide the RA patient relief from the symptoms.

In some embodiments, the lyophilized pharmaceutical compositions of the present invention can be used for treating diseases associated with abnormal hemoglobin synthesis. The method comprises administering the pharmaceutical formulations of the present invention to a patient suffering from disease associated with abnormal hemoglobin synthesis. Decitabine-containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In some embodiments, the lyophilized pharmaceutical compositions of the present invention can be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

In some embodiments, the lyophilized pharmaceutical compositions of the invention can be used in the treatment of patients with genetic mutations associated with tumor hypermethylation such as patients with tumor types which contain the succinate dehydrogenase (SDH) mutation or deficiency which includes patients with non-KIT mutated gastrointestinal stromal tumors (GIST).

Gene activation facilitated by the lyophilized pharmaceutical compositions of the present invention can induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Myelodysplastic syndromes (MDS) are heterogeneous clonal hematopoietic stem cell disorders associated with the presence of dysplastic changes in one or more of the hematopoietic lineages, including dysplastic changes in the myeloid, erythroid, and megakaryocytic series. These changes result in cytopenias in one or more of the three lineages. Subjects afflicted with MDS typically develop complications related to anemia, neutropenia (infections), or thrombocytopenia (bleeding). Generally, from about 10% to about 70% of subjects with MDS develop acute leukemia. Representative myelodysplastic syndromes include acute myeloid leukemia, acute promyelocytic leukemia, acute lymphoblastic leukemia, and chronic myelogenous leukemia.

Acute myeloid leukemia (AML) is the most common type of acute leukemia in adults. Several inherited genetic disorders and immunodeficiency states are associated with an increased risk of AML. These include disorders with defects in DNA stability leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15; 17 chromosomal translocation. This translocation leads to the generation of a fusion transcript comprising a retinoic acid receptor sequence and a promyelocytic leukemia sequence.

Acute lymphoblastic leukemia (ALL) is a heterogenous disease with distinct clinical features displayed by various subtypes. Reoccurring cytogenetic abnormalities have been demonstrated in ALL. The most common associated cytogenetic abnormality is the 9; 22 translocation leading to development of the Philadelphia chromosome.

In a particular embodiment, the the lyophilized pharmaceutical compositions of the present invention can be used to treat an MDS, for example an MDS selected from AML, APML and ALL.

It will be appreciated that in each of the foregoing therapeutic uses, the lyophilized pharmaceutical compositions of the invention will typically be reconstituted in a suitable solvent as defined herein before administration to a subject, e.g. a mammalian subject such as a human patient.
Dosing and Administration.

Doses of lyophilized pharmaceutical compositions of the invention, reconstituted or mixed as necessary with a pharmaceutically acceptable solvent or solvent mixture as defined herein can be administered to a subject by methods known in the art. Non-limiting examples of methods of administration include subcutaneous injection, intravenous injection, and infusion.

A dose of a formulation contains an amount that is therapeutically-effective for treating a disease. A therapeutically-effective amount of a compound of the invention can be expressed as mg of the compound per kg of subject body mass. In some embodiments, a therapeutically-effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, a therapeutically-effective amount is 5 mg/kg, 10 mg/kg, 25 mg/kg, 50 mg/kg, 75 mg/kg, 100 mg/kg, 150 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1,000 mg/kg, about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

A compound described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A compound described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

In some embodiments, a therapeutically-effective amount can be administered 1-35 times per week, 1-14 times per week, or 1-7 times per week. In some embodiments, a therapeutically-effective amount can be administered 1-10 times per day, 1-5 times per day, 1 time, 2 times, or 3 times per day.

It is envisaged that the lyophilized pharmaceutical compositions of the invention will be useful either alone or in combination therapy with other chemotherapeutic agents or radiation therapy in the prophylaxis or treatment of a range of proliferative disease states or conditions. Examples of such disease states and conditions are set out above.

The lyophilized pharmaceutical compositions of the invention, whether administered alone, or in combination with anti-cancer agents and therapies such as radiotherapy, are generally administered to a subject in need of such administration, for example a human or animal patient, preferably a human.

Examples of chemotherapeutic agents that can be co-administered with the lyophilized pharmaceutical compositions of the invention as defined herein include but are not limited to topoisomerase I inhibitors; other antimetabolites; tubulin targeting agents; DNA binder and topoisomerase II inhibitors; alkylating agents; monoclonal antibodies; anti-hormones; signal transduction inhibitors; proteasome inhibitors; DNA methyl transferase inhibitors; cytokines; interferons; interleukins; retinoids; chromatin targeted therapies, e.g. HDAC or HAT modulators; T-cell activating agents, including immunomodulating antibodies; cancer vaccines; hormonal agents; plant-derived agents; biologic agents; immunomodulating agents; radiotherapy; and other therapeutic or prophylactic agents; for example agents that reduce or alleviate some of the side effects associated with chemotherapy; for example anti-emetic agents and agents that prevent or decrease the duration of chemotherapy-associated neutropenia and prevent complications that arise from reduced levels of red blood cells or white blood cells, such as erythropoietin (EPO), granulocyte macrophage-colony stimulating factor (GM-CSF), and granulocyte-colony stimulating factor (G-CSF).

In one embodiment, the lyophilized pharmaceutical compositions of the invention are used in combination with (or further comprise) inhibitors of histone deacetylase (HDAC) to further modulate transcription of genes, e.g., to reestablish transcription of genes silenced by hypermethylation and acetylation of histones, in a synergistic manner.

Inhibitors of HDACs include, but are not limited to, the following structural classes: 1) hydroxamic acids, 2) cyclic peptides, 3) benzamides, and 4) short-chain fatty acids. Examples of hydroxamic acids and hydroxamic acid derivatives, include trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. TSA was isolated as an antifungi antibiotic (Tsuji et al (1976) J. Antibiot (Tokyo) 29:1-6) and found to be a potent inhibitor of mammalian HDAC (Yoshida et al. (1990) J. Biol. Chem. 265:17174-17179). The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. Glick et al. (1999) Cancer Res. 59:4392-4399. These hydroxamic acid-based HDAC inhibitors all possess an essential structural feature: a polar hydroxamic terminal linked through a hydrophobic methylene spacer (e.g. 6 carbon at length) to another polar site which is attached to a terminal hydrophobic moiety (e.g., benzene ring).

Cyclic peptides used as HDAC inhibitors are mainly cyclic tetrapeptides. Examples of cyclic peptides include, but are not limited to, trapoxin A, apicidin and FR901228. Trapoxin A is a cyclic tetrapeptide that contains a 2-amino-8-oxo-9,10-epoxy-decanoyl (AOE) moiety. Kijima et al. (1993) J. Biol. Chem. 268:22429-22435. Apicidin is a fungal metabolite that exhibits potent, broad-spectrum antiprotozoal activitity and inhibits HDAC activity at nanomolar concentrations. Darkin-Rattray et al. (1996) Proc. Natl. Acad. Sci. USA. 93; 13143-13147. FR901228 is a depsipeptide that is isolated from Chromobacterium violaceum, and has been shown to inhibit HDAC activity at micromolar concentrations.

Examples of benzamides include but are not limited to MS-27-275. Saito et al. (1990) Proc. Natl. Acad. Sci. USA. 96:4592-4597. Examples of short-chain fatty acids include but are not limited to butyrates (e.g., butyric acid, arginine butyrate and phenylbutyrate (PB)). Newmark et al. (1994) Cancer Lett. 78:1-5; and Carducci et al. (1997) Anticancer Res. 17:3972-3973. In addition, depudecin which has been shown to inhibit HDAC at micromolar concentrations (Kwon et al. (1998) Proc. Natl. Acad. Sci. USA. 95:3356-3361) also falls within the scope of histone deacetylase inhibitor of the present invention.

In one embodiment, an alkylating agent is used in combination with the lyophilized pharmaceutical compositions of the invention. Examples of alkylating agents include bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin).

In another embodiment the lyophilized pharmaceutical composition of the invention is used in combination with a platinum compound such as cisplatin or carboplatin.

In another embodiment, the lyophilized pharmaceutical composition of the invention is used in combination with a member of the retinoids superfamily such as all-trans-retinol, all-trans-retinoic acid (tretinoin), 13-cis retinoic acid (isotretinoin) and 9-cis-retinoic acid.

In a further embodiment, the lyophilized pharmaceutical composition of the invention is used in combination with a hormonal agent such as a synthetic oestrogen (e.g. diethylstibestrol), antiestrogen (e.g. tamoxifen, toremifene, fluoxymesterol and raloxifene), antiandrogen (bicalutamide, nilutamide, flutamide), aromatase inhibitor (e.g., aminoglutethimide, anastrozole and tetrazole), ketoconazole, goserelin acetate, leuprolide, megestrol acetate and mifepristone.

In yet another embodiment, the lyophilized pharmaceutical composition of the invention is used in combination with a plant-derived agent such as a vinca alkaloid (e.g., vincristine, vinblastine, vindesine, vinzolidine and vinorelbine), camptothecin (20(S)-camptothecin, 9-nitro-20(S)-camptothecin, and 9-amino-20(S)-camptothecin), a podophyllotoxin (e.g., etoposide (VP-16) and teniposide (VM-26)), and taxane (e.g., paclitaxel and docetaxel).

In a particular embodiment, the lyophilized pharmaceutical composition of the invention is used in combination with a taxane such as paclitaxel and docetaxel.

In another embodiment, lyophilized pharmaceutical compositions of the invention can be used in combination with an anthracycline, such as daunorubicin or idarubicin.

In a further embodiment, the lyophilized pharmaceutical composition of the invention is used in combination with a biological agent such as an immuno-modulating protein (e.g. a cytokine), a monoclonal antibody against a tumour antigen, a tumour suppressor gene or a cancer vaccine.

Examples of interleukins that can be used in combination with the lyophilized pharmaceutical composition of the invention include, but are not limited to, interleukin 2 (IL-2), and interleukin 4 (IL-4), interleukin 12 (IL-12). Examples of interferons that can be used in conjunction with the lyophilized pharmaceutical composition of the invention include, but are not limited to, interferon [alpha], interferon [beta](fibroblast interferon) and interferon [gamma] (fibroblast interferon). Examples of such cytokines include, but are not limited to erythropoietin (epoietin), granulocyte-CSF (filgrastim), and granulocyte, macrophage-CSF (sargramostim) Immuno-modulating agents other than cytokines include, but are not limited to bacillus Calmette-Guerin, levamisole, and octreotide.

Examples of monoclonal antibodies against tumour antigens that can be used in conjunction with the the lyophilized pharmaceutical composition of the invention include, but are not limited to, HERCEPTIN® (Trastruzumab), RITUXAN® (Rituximab), MYLOTARG® (anti-CD33), and CAMPATH® (anti-CD52).

In a further embodiment, the lyophilized pharmaceutical composition of the invention can be used in combination with a cancer vaccine, for example a cancer vaccine selected from a CTA cancer vaccine, such as a vaccine based on a CTA antigen selected from: NY-ESO-1, LAGE-1, MAGE-A1, -A2, -A3, -A4, -A6, -A10, -A12, CT7, CT10, GAGE1-6, GAGE 1-2, BAGE, SSX1-5, SSX 2, HAGE, PRAME, RAGE-1, XAGE-1, MUC2, MUC5B and HMW-MAA. Non-limiting examples of CTA vaccines include those based on MAGE-A3 (for example recMAGE-A3), NY-ESO-1 and PRAME.

In another embodiment, the lyophilized pharmaceutical composition of the invention can be used in combination with a T-cell activating agent, for example a T-cell activating agent which is an antibody (optionally a mAb), for example selected from: (a) a CD137 agonist; (b) a CD40 agonist; (c) an OX40 agonist; (d) a PD-1 mAb; (e) a PD-L1 mAb; (I) a CTLA-4 mAb; and (g) combinations of (a)-(f). In some embodiments, the ancillary therapeutic component is Tremelimumab or Ipilimumab.

In another embodiment, the the lyophilized pharmaceutical composition of the invention can be used in combination with carboplatin for the treatment of platinum-resistant recurrent ovarian cancer.

In another embodiment, the lyophilized pharmaceutical composition of the invention can be used in the treatment of hepatocellular carcinoma (e.g. post sorafenib failures).

In another embodiment, the lyophilized pharmaceutical composition of the invention can be used in combination with irinotecan for the treatment of metastatic colon cancer.

In another embodiment, the lyophilized pharmaceutical composition of the invention can be used in combination with 5-fluorouracil (5-FU), leucovorin, oxaliplatin for the treatment of metastatic colon cancer.

In another embodiment, the lyophilized pharmaceutical composition of the invention can be used in combination with cytarabine and fludarabine for the treatment of pediatric relapsed/refractory AML.

In another embodiment, the lyophilized pharmaceutical composition of the invention can be used in combination with a JAK2 inhibitor for the treatment of myoproliferative neoplasms.

The lyophilized pharmaceutical composition of the invention and any other therapeutic agents can be presented separately or presented together in a pharmaceutical package, kit or patient pack.

The lyophilized pharmaceutical composition of the invention and combinations with other therapeutic agents or radiation therapies as described above can be administered over a prolonged term to maintain beneficial therapeutic effects or can be administered for a short period only. Alternatively, they can be administered in a pulsatile or continuous manner.

The lyophilized pharmaceutical composition of the invention can be administered in an effective amount, i.e. an amount that is effective to bring about the desired therapeutic effect either alone (in monotherapy) or in combination with one or more chemotherapeutic agents or radiation therapy. For example, the "effective amount" can be a quantity of compound which, when administered to a subject suffering from cancer, slows tumour growth, ameliorates the symptoms of the disease and/or increases longevity.

The amount of the lyophilized pharmaceutical composition of the invention administered to the subject can depend on the type and severity of the disease or condition and on the characteristics of the subject, such as general health, age, sex, body weight and tolerance to drugs. The skilled person is able to determine appropriate dosages depending on these and other factors. Effective dosages for commonly used anti-cancer drugs and radiation therapy are well known to the skilled person.

Purity of Compounds of the Invention.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

EXAMPLES

Example 1. Preparation of a Lyophilized Formulation of a Sodium Salt of the Compound of Formula (1)

The sodium salt of the compound of formula (1) was dissolved in DMSO at a defined concentration using an overhead mixer in an appropriately sized stainless steel (SS) vessel. Upon complete solubilization of the drug in DMSO, samples of the bulk solution were tested using a UV or HPLC in-process method to determine that the amount of the sodium salt of the compound of formula 1 was within 95-105% of the target concentration. The bulk solution was filtered through a series of two pre-sterilized 0.2 micron sterilizing filters that were DMSO-compatible, and collected into a 2 L SS surge vessel. The filtration rate was continuously adjusted by visual monitoring of quantity available for filling in the surge vessel. One gram aliquots of the filtered bulk solution were then filled into 5 cc depyrogenated, clear glass vials. Each vial was automatically and partially stoppered on the fill line with a fluoropolymer coated, chlorobutyl rubber lyo stopper that was pre-sterilized. The product vials were transferred to a lyophilizer under aseptic transfer conditions for initiation of a lyophilization cycle. The lyophilizer used was a pilot scale lyophilizer, Lyobeta 35, IMA-Telstar, which has 1.02 m$^2$ of chamber space, an ice capacity of 35 kg, 22 kg/24 hr for condenser capacity.

Vials containing the solution were lyophilized using the cycle parameters set out below in TABLE 1.

TABLE 1

Lyophilization cycle operating parameters

| Stage | Event | T (° C.) | P | Time (h) |
|---|---|---|---|---|
| | Load | 5 | Atm | 0.0 |
| First freezing stage | Ramp temperature | −45 | Atm | 1.0 |
| First freezing stage | Hold temperature | −45 | Atm | 1.5 |
| First warming stage | Ramp temperature | 0 | Atm | 1.3 |
| First warming stage | Hold temperature | 0 | Atm | 2.0 |
| Second freezing stage | Ramp temperature | −45 | Atm | 2.0 |
| Second freezing stage | Hold temperature | −45 | Atm | 2.0 |
| Primary drying stage | Decrease and hold pressure | −45 | 6 µbar | 4.0 |
| Primary drying stage | Ramp temperature | −20 | 6 µbar | 3.0 |
| Primary drying stage | Hold temperature | −20 | 6 µbar | 12.0 |
| Primary drying stage | Ramp temperature | −5 | 6 µbar | 3.0 |
| Primary drying stage | Hold temperature | −5 | 6 µbar | 24.0 |
| Secondary drying stage | Ramp temperature | 65 | 6 µbar | 6.0 |
| Secondary drying stage | Hold temperature | 65 | 6 µbar | 15.0 |

Upon completion of the lyophilization cycle, the lyophilizer was back-filled with nitrogen, and the vials were completely and automatically stoppered. Vials were aseptically transferred to an isolator where each of the vials was automatically capped with a blue aluminum flip-off cap. Vials were visually inspected before proceeding with sampling for release testing, and the labeling and packaging operation. Vials were kept at 2-8° C. until ready. Each vial was labeled for its content.

Example 2. Comparative Tests

I. Lyophilized Formulations Made by the Process of the Invention:

Bulk solutions were made containing the sodium salt of the compound of formula (1) at four different concentrations in DSMO and the resulting solutions (designated A to D) were filled into lyophilization vials and subjected to lyophilization using the protocol described above in Example 1. Pirani and Baratron gauges were used to determine the end of the primary drying (sublimation) stage. FIG. 1 shows the progressive reduction in DMSO content over time during the primary and secondary drying stages.

Following lyophilization, the lyophilized samples were analysed for purity (% purity by HPLC), DMSO residual content, and residual moisture. The samples were reconstituted by dissolving them in the non-aqueous solvent system described in TABLE 2 below and the reconstitution time and appearance of the reconstituted formulations were analysed.

TABLE 2

Solvent for reconstitution

| | % of each ingredient | Grade | Function |
|---|---|---|---|
| Propylene glycol | 65 | NF, PhEur | Solvent |
| Glycerin | 25 | NF, PhEur | Solvent |
| Alcohol/Ethanol | 10 | USP, PhEur | Thinning agent |

The results of the analyses are set out in TABLE 3 below. Results for four different concentrations, n=1

TABLE 3

| | Sample ID | | | |
|---|---|---|---|---|
| Analysis | A (100 mg/mL) | B (75 mg/mL) | C (50 mg/mL) | D (25 mg/mL) |
| % Purity by HPLC (API purity 93.6%) | 93.2 | 93.1 | 93.2 | 93.2 |
| DMSO residual solvent % | 19.4 | 15.1 | 19.2 | 20.8 |
| Residual Moisture | <LOQ | <LOQ | <LOQ | <LOQ |
| Reconstitution time (manual) | 17 min 40 s | 12 min 51 s | 12 min 49 s | 18 min 51 s |
| Appearance of the reconstituted solution | Clear solution, slightly yellow | | | |

LOQ = limit of quantitation

II. Comparative Formulations:

Bulk solutions of the sodium salt of the compound of formula (1) at a concentration of 100 mg/mL were subjected to lyophilization using the apparatus described in Example 1 above but a different temperature profile which did not include the first warming stage during the freezing of the solution but included freezing the formulation at different freezing rates. The characteristics of the Comparative formulations prepared in this way are shown in TABLE 4 below.

TABLE 4

| | | Identification N° | | |
|---|---|---|---|---|
| Analysis | Specification | FP1 | FP2 | FP3 |
| | | | Result | |
| Appearance of the cake (all vials) | Description | Compact cake detached from the walls | Compact cake detached from the walls | Firm cake with cracks adhering to the bottom of the vial |
| Appearance of the | Clear solution free of particles | Clear solution with particles sticking to | Clear solution with particles sticking to | Clear solution with particles sticking to |

TABLE 4-continued

| | | Identification N° | | |
|---|---|---|---|---|
| | | FP1 | FP2 | FP3 |
| Analysis | Specification | | Result | |
| reconstituted solution and time for reconstitution | | the walls >30 min for complete dissolution | the walls >30 min for complete dissolution | the wall >30 min for complete dissolution |
| Water content | Below 1% (tentative) | 0.02% | 0.005% | 0.001% |
| Residual Solvent DMSO | Report result for information | 19.1% (FP1-9) | 19.4% (FP2-9) | 19.4% (FP3-9) |

III. Comparison of Results Obtained from the Formulations Described in I and II

The results shown in step I above demonstrate that when an intermediate warming stage ("first warming stage") is included during the freezing of the solution prior to primary drying in accordance with the invention, the result is a lyophilized dry formulation which can be reconstituted in under 20 minutes and under 15 minutes in some cases.

By comparison, the Comparative formulations FP1, FP2 and FP3 described in II above, made by a process that omitted the intermediate warming stage, took longer to reconstitute (over 30 minutes). Without wishing to be bound by any theory, it is believed that the intermediate warming stage has the effect of increasing the porosity of the lyophilized product and increasing the surface area available for contact with solvent molecules, thereby increasing the solubility of the formulations.

IV. Comparison of Drying Times with Example 4 in WO2013/033176

Example 4 in WO2013/033176 describes the lyophilization of a solution of the sodium salt of the compound of formula (1) using the cycle parameters shown in TABLE 5 below.

TABLE 5

| Stage | Event | T (° C.) | Temperature/Pressure/Time P | Time (minutes) |
|---|---|---|---|---|
| Freezing stage | Ramp temperature | −40 | Atm | 133 |
| Freezing stage | Hold temperature | −40 | Atm | 360 |
| Primary drying stage | Ramp temperature and pressure | −5 | 100 mTorr | 117 |
| Primary drying stage | Hold temperature and pressure | −5 | 100 mTorr | 1440 |
| Primary drying stage | Ramp temperature | 10 | 100 mTorr | 50 |
| Primary drying stage | Hold temperature | 10 | 100 mTorr | 1440 |
| Secondary drying stage | Ramp temperature and pressure | 30 | 50 mTorr | 67 |
| Secondary drying stage | Hold temperature and pressure | 30 | 50 mTorr | 1440 |
| Secondary drying stage | Ramp temperature | 60 | 50 mTorr | 100 |
| Secondary drying stage | Hold temperature | 60 | 50 mTorr | 1440 |
| Total lyophilization time | 6587 minutes = 109 hours and 47 minutes | | | |

The total lyophilization time for the formulation described in Example 4 of WO2013/033176 is 109 hours and 47 minutes. By comparison, the total lyophilization time for the formulation of the invention as described in I above was 76.8 hours, i.e. over 30 hours shorter than the total lyophilization time for Example 4 in WO2013/033176. Most of the difference is accounted for by the significantly reduced secondary drying stage of the process of the present invention compared to the process described in Example 4 of WO2013/033176 (21 hours vs 50.78 hours). In the process of the present invention, an intermediate (first) warming stage is interposed between two freezing stages when the solution is initially frozen, and this is believed to result in a much more porous structure from which DMSO can more readily sublime during the primary drying stage. Thus, a greater proportion of the DMSO is removed during the primary drying stage with the result that much shorter secondary drying stage can be employed.

Therefore, in summary, the process of the present invention can reduce the time necessary to produce a lyophilized product that has greatly enhanced dissolution characteristics.

Example 3. Larger Scale Studies on the 75 mg/ml and 100 mg/ml Formulations A and B The results obtained in the experiments described in Example 2 showed that the lowest residual DMSO levels were obtained with formulation B in which a bulk solution containing a concentration of 75 mg/mL of active compound was lyophilized. Confirmatory studies were therefore carried out on 75 mg/ml and 100 mg/ml solutions of the sodium salt of the compound of formula (1) in DMSO. The lyophilization was carried out at a 100 vial scale, and analysis was carried out on multiple samples. The protocol used was as described in Example 1. The properties of the resulting lyophilized products were as shown in TABLE 6 below.

TABLE 6

| | Sample ID | |
|---|---|---|
| Analysis | 100 mg/mL | 75 mg/mL |
| Residual DMSO % w/w, n = 3 | 17.4 (24.2 mg/vial) | 18.7% (25.4 mg/vial) |
| Reconstitution time (min), n = 3 | 8 min* | 8 min* |
| Appearance, n = 3 | Clear and colourless** | |
| Water Content, n = 2 | <LOQ | <LOQ |
| Assay % w/w, n = 2 | 107.8 | 105 |

*The reconstitution time does not include dissipation of bubbles which might take about an additional 10 minutes. However, the reconstitution was carried out manually and did not require mechanised mixing apparatus.
**Although not seen in this instance, there can be occasions when the solutions are slightly hazy and/or slightly off-white to yellow in color.

The results in TABLE 6 demonstrate that the process of the invention can be used to prepare lyophilized formulations that have a reconstitution time of less than ten minutes (excluding the time taken for bubbles to clear) and that reconstitution can be carried out manually without the need for mechanized mixers.

Example 4. Preparation of the Sodium Salt of the Compound of Formula (1)

The sodium salt of the compound of formula (1) was prepared as described in U.S. Pat. No. 7,700,567 (the content of which is hereby incorporated by reference) by coupling 1s (where $R_1$=carbamate protective group) with phosphoramidite building block 1d:

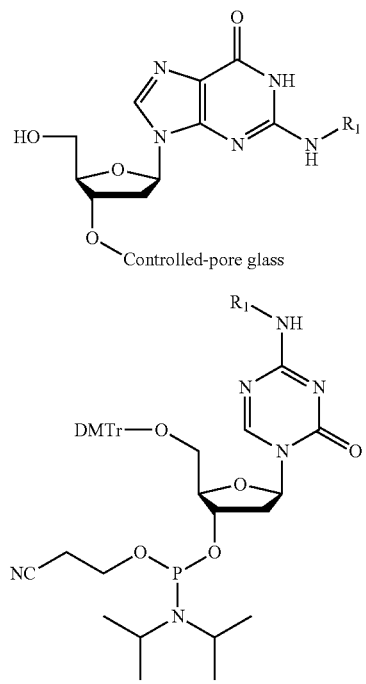

A protected 2'-deoxyguanosine-linked CPG solid support 1s (where $R_1$=tert-butyl phenoxyacetyl) was coupled with 2-2.5 equivalents of phenoxyacetyl decitabine phosphoramidite (1d, where $R_1$=phenoxyacetyl) in the presence of 60% of 0.3 M benzylthiotetrazole activator (in acetonitrile) for 10 minutes. The CPG solid support containing protected DpG dinucleotide was treated with 20 mL of 50 mM $K_2CO_3$ in methanol for 1 hour and 20 minutes. The coupled product was oxidized, the protective group was removed, and the resultant compound was washed, filtered, and purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes.

The ESI-MS (−ve) of DpG dinucleotide 2b:

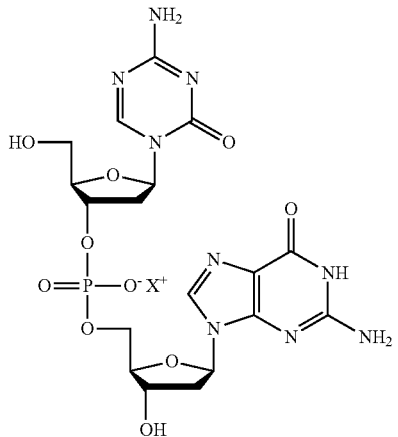

where $X^+$=triethylammonium (calculated exact mass for the neutral compound $C_{18}H_{24}N_9O_{10}P$ is 557.14), exhibited m/z 556.1 [M-H]$^-$ and 1113.1 for [2M-H]$^-$ (see mass spectrum in FIG. 31 of U.S. Pat. No. 7,700,567).

The sodium salt of the compound of formula (1), i.e. DpG dinucleotide 2b, where $X^+$=sodium, was obtained by re-dissolving the triethylammonium salt in 4 mL water, 0.2 mL 2M $NaClO_4$ solution. When 36 mL acetone was added, the dinucleotide precipitated. The solution was kept at −20° C. for several hours and centrifugated at 4000 rpm for 20 minutes. The supernatant was discarded and the solid was washed with 30 mL acetone followed by an additional centrifugation at 4000 rpm for 20 minutes. The precipitate, which was dissolved in water and freeze dried, exhibited m/z 556.0 [M-H]$^-$ (see mass spectrum in FIG. 36 of U.S. Pat. No. 7,700,567).

EMBODIMENTS

The following non-limiting embodiments provide illustrative examples of the invention, but do not limit the scope of the invention.

Embodiment 1

A method of preparing a lyophilized pharmaceutical composition, the method comprising dissolving a compound of formula (1):

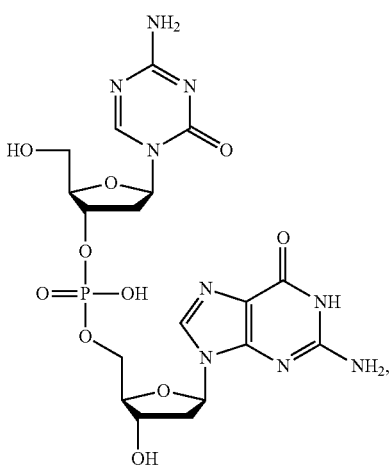

(1)

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature thereof to a temperature of no greater than about −20° C.; (ii) a first warming stage in which the temperature of the frozen solution is raised to a temperature in the range from about −15° C. to about 5° C., wherein the temperature in the range from about −15° C. to about 5° C. keeps the solution frozen; (iii) a second freezing stage in which the temperature of the solution is lowered to a temperature of no greater than about −20° C.; (iv) a primary drying stage, wherein the primary drying stage comprises a sublimation step in which the DMSO is removed by sublimation from the solution in its frozen state under reduced pressure to give a partially dried product; and (v) a secondary drying stage in which the DMSO is removed by evaporation from the partially dried product in a non-frozen state under reduced pressure to give the lyophilized product.

Embodiment 2

The method of embodiment 1, wherein the compound of formula (1) is in the form of a sodium salt.

Embodiment 3

The method of any one of embodiments 1-2, wherein the solvent is non-aqueous.

Embodiment 4

The method of any one of embodiments 1-3, wherein the lyophilized pharmaceutical composition has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

Embodiment 5

The method of any one of embodiments 1-4, wherein in an amount of the lyophilized pharmaceutical composition obtained from 1 gram of the solution, there is a residual DMSO content of no greater than about 20 mg.

Embodiment 6

The method of any one of embodiments 1-5, wherein any residual DMSO present in the lyophilized pharmaceutical composition is in an amount corresponding to no more than 35 mg per 100 mg equivalent of a free base of the compound of formula (1).

Embodiment 7

The method of any one of embodiments 1-6, further comprising packing the lyophilized pharmaceutical in a sealed pharmaceutical container.

Embodiment 8

The method of any one of embodiments 1-7, further comprising dissolving the lyophilized pharmaceutical composition in a solvent to form an injectable liquid composition.

Embodiment 9

The method of embodiment 8, wherein the solvent is a non-aqueous solvent.

Embodiment 10

The method of any one of embodiments 1-9, wherein the solution further comprises a co-solvent.

Embodiment 11

The method of embodiment 1, further comprising reconstituting the lyophilized pharmaceutical composition in a pharmaceutically acceptable solvent to give a liquid formulation containing a compound of formula (1) or the pharmaceutically acceptable salt thereof.

Embodiment 12

The method of any one of embodiments 1-11, wherein the reduced pressure in the primary drying stage is from about 5 µBar to about 40 µBar.

Embodiment 13

The method of any one of embodiments 1-12, wherein the temperature in the primary drying stage is from about −3° C. to about −9° C.

Embodiment 14

The method of any one of embodiments 1-13, wherein the temperature in the secondary drying stage is from about 30° C. to about 65° C.

Embodiment 15

A pharmaceutical composition prepared by a process comprising the steps of: dissolving a compound of formula (1):

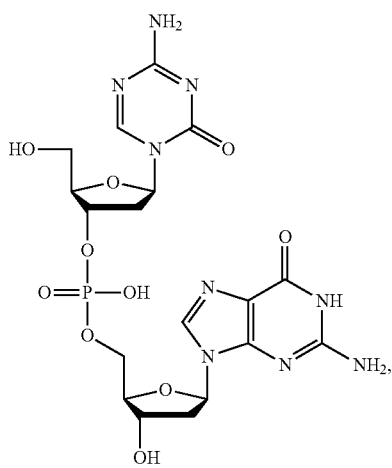

(1)

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature thereof to a temperature of no greater than about −20° C.; (ii) a first warming stage in which the temperature of the frozen solution is raised to a temperature in the range from about −15° C. to about 5° C., wherein the temperature in the range from about −15° C. to about 5° C. keeps the solution frozen; (iii) a second freezing stage in which the temperature of the solution is lowered to a temperature of no greater than about −20° C.; (iv) a primary drying stage, wherein the primary drying stage comprises a sublimation step in which the DMSO is removed by sublimation from the solution in its frozen state under reduced pressure to give a partially dried product; and (v) a secondary drying stage in which the DMSO is removed by evaporation from the partially dried product in a non-frozen state under reduced pressure to give the lyophilized product.

Embodiment 16

The pharmaceutical composition of embodiment 15, wherein the compound of formula (1) is in the form of a sodium salt.

Embodiment 17

The pharmaceutical composition of any one of embodiments 15-16, wherein the solvent is non-aqueous.

Embodiment 18

The pharmaceutical composition of any one of embodiments 15-17, wherein the lyophilized pharmaceutical composition has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

Embodiment 19

The pharmaceutical composition of any one of embodiments 15-18, wherein in an amount of the lyophilized pharmaceutical composition obtained from 1 gram of the solution, there is a residual DMSO content of no greater than about 20 mg.

Embodiment 20

The pharmaceutical composition of any one of embodiments 15-19, wherein any residual DMSO present in the lyophilized pharmaceutical composition is in an amount corresponding to no more than 35 mg per 100 mg equivalent of a free base of the compound of formula (1).

Embodiment 21

The pharmaceutical composition of any one of embodiments 15-20, the process further comprising packing the lyophilized pharmaceutical in a sealed pharmaceutical container.

Embodiment 22

The pharmaceutical composition of any one of embodiments 15-21, the process further comprising dissolving the lyophilized pharmaceutical composition in a solvent to form an injectable liquid composition.

Embodiment 23

The pharmaceutical composition of embodiment 22, wherein the solvent is a non-aqueous solvent.

Embodiment 24

The pharmaceutical composition of any one of embodiments 15-23, wherein the solution further comprises a co-solvent.

Embodiment 25

The pharmaceutical composition of embodiment 15, the process further comprising reconstituting the lyophilized pharmaceutical composition in a pharmaceutically acceptable solvent to give a liquid formulation containing a compound of formula (1) or the pharmaceutically acceptable salt thereof.

Embodiment 26

The pharmaceutical composition of any one of embodiments 15-25, wherein the reduced pressure in the primary drying stage is from about 5 µBar to about 40 µBar.

Embodiment 27

The pharmaceutical composition of any one of embodiments 15-26, wherein the temperature in the primary drying stage is from about −3° C. to about −9° C.

Embodiment 28

The pharmaceutical composition of any one of embodiments 15-27, wherein the temperature in the secondary drying stage is from about 30° C. to about 65° C.

What is claimed is:
1. A method of preparing a lyophilized pharmaceutical product, the method comprising dissolving a compound of formula (1):

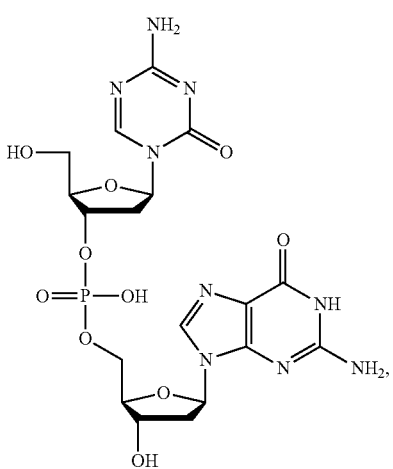

or a pharmaceutically-acceptable salt thereof, in a solvent comprising dimethylsulfoxide (DMSO) to form a solution, wherein the solvent is then removed by a freeze-drying process to give the lyophilized pharmaceutical product, wherein the freeze-drying process comprises:
(i) a first freezing stage in which the solution is frozen by reducing the temperature thereof to a temperature of no greater than about −20° C.;
(ii) a first warming stage in which the temperature of the frozen solution is raised to a temperature in the range from about −15° C. to about 5° C., wherein the temperature in the range from about −15° C. to about 5° C. keeps the solution frozen;
(iii) a second freezing stage in which the temperature of the solution is lowered to a temperature of no greater than about −20° C.;
(iv) a primary drying stage, wherein the primary drying stage comprises a sublimation step in which the DMSO is removed by sublimation from the solution in its frozen state under reduced pressure to give a partially dried product, wherein the reduced pressure in the primary drying stage is from about 5 µBar to about 40 µBar; and
(v) a secondary drying stage in which the DMSO is removed by evaporation from the partially dried product in a non-frozen state under reduced pressure to give the lyophilized pharmaceutical product.

2. The method of claim 1, wherein the compound of formula (1) is in the form of a sodium salt.

3. The method of claim 1, wherein the solvent is non-aqueous.

4. The method of claim 1, wherein the lyophilized pharmaceutical product has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

5. The method of claim 1, wherein in an amount of the lyophilized pharmaceutical product obtained from 1 gram of the solution, there is a residual DMSO content of no greater than about 20 mg.

6. The method of claim 1, wherein any residual DMSO present in the lyophilized pharmaceutical product is in an amount corresponding to no more than 35 mg per 100 mg equivalent of a free base of the compound of formula (1).

7. The method of claim 1, further comprising packing the lyophilized pharmaceutical product in a sealed pharmaceutical container.

8. The method of claim 1, further comprising dissolving the lyophilized pharmaceutical product in another solvent to form an injectable liquid composition.

9. The method of claim 8, wherein the another solvent is a non-aqueous solvent.

10. The method of claim 1, wherein the solution further comprises a co-solvent.

11. The method of claim 1, further comprising reconstituting the lyophilized pharmaceutical product in a pharmaceutically acceptable solvent to give a liquid formulation containing a compound of formula (1) or the pharmaceutically acceptable salt thereof.

12. The method of claim 1, wherein the temperature in the primary drying stage is from about −3° C. to about −9° C.

13. The method of claim 1, wherein the temperature in the secondary drying stage is from about 30° C. to about 65° C.

14. A pharmaceutical product prepared by a process comprising the steps of:
dissolving a compound of formula (1):

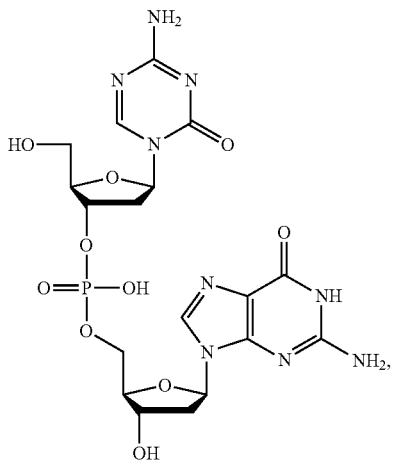

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises:
(i) a first freezing stage in which the solution is frozen by reducing the temperature thereof to a temperature of no greater than about −20° C.;
(ii) a first warming stage in which the temperature of the frozen solution is raised to a temperature in the range from about −15° C. to about 5° C., wherein the temperature in the range from about −15° C. to about 5° C. keeps the solution frozen;
(iii) a second freezing stage in which the temperature of the solution is lowered to a temperature of no greater than about −20° C.;
(iv) a primary drying stage, wherein the primary drying stage comprises a sublimation step in which the DMSO is removed by sublimation from the solution in its frozen state under reduced pressure to give a partially dried product; and
(v) a secondary drying stage in which the DMSO is removed by evaporation from the partially dried product in a non-frozen state under reduced pressure to give the lyophilized product,
wherein any residual DMSO present in the lyophilized product is in an amount corresponding to no more than 35 mg per 100 mg equivalent of a free base of the compound of formula (1).

15. A method of preparing a lyophilized pharmaceutical product, the method comprising dissolving a compound of formula (1):

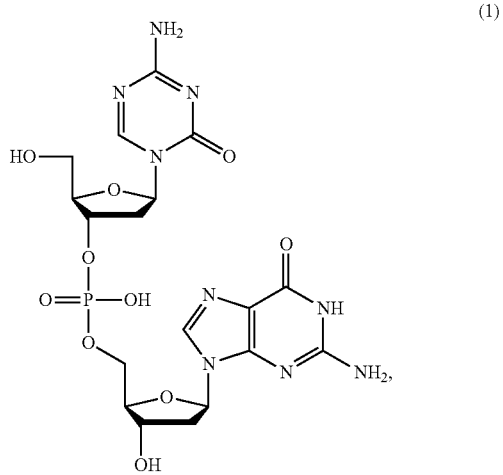

(1)

or a pharmaceutically-acceptable salt thereof, in a solvent comprising dimethylsulfoxide (DMSO) to form a solution, wherein the solvent is then removed by a freeze-drying process to give the lyophilized pharmaceutical product, wherein the freeze-drying process comprises:
(i) a first freezing stage in which the solution is frozen by reducing the temperature thereof to a temperature of no greater than about −20° C.;
(ii) a first warming stage in which the temperature of the frozen solution is raised to a temperature in the range from about −15° C. to about 5° C., wherein the temperature in the range from about −15° C. to about 5° C. keeps the solution frozen;
(iii) a second freezing stage in which the temperature of the solution is lowered to a temperature of no greater than about −20° C.;
(iv) a primary drying stage, wherein the primary drying stage comprises a sublimation step in which the DMSO is removed by sublimation from the solution in its frozen state under reduced pressure to give a partially dried product; and
(v) a secondary drying stage in which the DMSO is removed by evaporation from the partially dried product in a non-frozen state under reduced pressure to give the lyophilized pharmaceutical product,
wherein in an amount of the lyophilized pharmaceutical product obtained from 1 gram of the solution, there is a residual DMSO content of no greater than about 20 mg.

16. The method of claim 15, wherein the compound of formula (1) is in the form of a sodium salt.

17. The method of claim 15, wherein the solvent is non-aqueous.

18. The method of claim 15, wherein the lyophilized pharmaceutical product has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

19. The method of claim 15, further comprising packing the lyophilized pharmaceutical product in a sealed pharmaceutical container.

20. The method of claim 15, further comprising dissolving the lyophilized pharmaceutical product in another solvent to form an injectable liquid composition.

21. The method of claim 20, wherein the another solvent is a non-aqueous solvent.

22. The method of claim 15, wherein the solution further comprises a co-solvent.

23. The method of claim 15, further comprising reconstituting the lyophilized pharmaceutical product in a pharmaceutically acceptable solvent to give a liquid formulation containing a compound of formula (1) or the pharmaceutically acceptable salt thereof.

24. The method of claim 15, wherein the temperature in the primary drying stage is from about −3° C. to about −9° C.

25. The method of claim 15, wherein the temperature in the secondary drying stage is from about 30° C. to about 65° C.

26. A method of preparing a lyophilized pharmaceutical product, the method comprising dissolving a compound of formula (1):

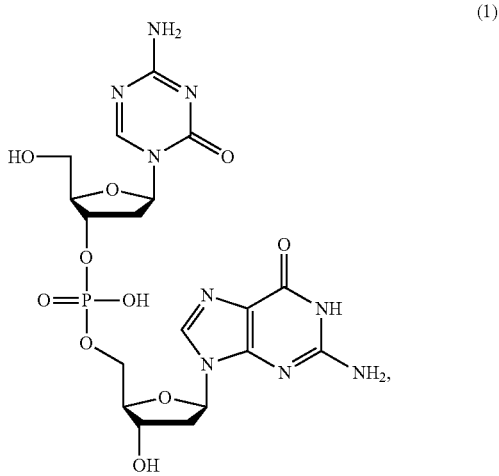

(1)

or a pharmaceutically-acceptable salt thereof, in a solvent comprising dimethylsulfoxide (DMSO) to form a solution, wherein the solvent is then removed by a freeze-drying process to give the lyophilized pharmaceutical product, wherein the freeze-drying process comprises:
(i) a first freezing stage in which the solution is frozen by reducing the temperature thereof to a temperature of no greater than about −20° C.;
(ii) a first warming stage in which the temperature of the frozen solution is raised to a temperature in the range from about −15° C. to about 5° C., wherein the temperature in the range from about −15° C. to about 5° C. keeps the solution frozen;
(iii) a second freezing stage in which the temperature of the solution is lowered to a temperature of no greater than about −20° C.;
(iv) a primary drying stage, wherein the primary drying stage comprises a sublimation step in which the DMSO is removed by sublimation from the solution in its frozen state under reduced pressure to give a partially dried product; and (v) a secondary drying stage in which the DMSO is removed by evaporation from the partially dried product in a non-frozen state under reduced pressure to give the lyophilized pharmaceutical product, wherein any residual DMSO present in the lyophilized pharmaceutical product is in an amount corresponding to no more than 35 mg per 100 mg equivalent of a free base of the compound of formula (1).

27. The method of claim 26, wherein the compound of formula (1) is in the form of a sodium salt.

28. The method of claim 26, wherein the solvent is non-aqueous.

29. The method of claim 26, wherein the lyophilized pharmaceutical product has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

30. The method of claim 26, further comprising packing the lyophilized pharmaceutical product in a sealed pharmaceutical container.

31. The method of claim 26, further comprising dissolving the lyophilized pharmaceutical product in another solvent to form an injectable liquid composition.

32. The method of claim 31, wherein the another solvent is a non-aqueous solvent.

33. The method of claim 26, wherein the solution further comprises a co-solvent.

34. The method of claim 26, further comprising reconstituting the lyophilized pharmaceutical product in a pharmaceutically acceptable solvent to give a liquid formulation containing a compound of formula (1) or the pharmaceutically acceptable salt thereof.

35. The method of claim 26, wherein the temperature in the primary drying stage is from about −3° C. to about −9° C.

36. The method of claim 26, wherein the temperature in the secondary drying stage is from about 30° C. to about 65° C.

* * * * *